(12) United States Patent
Tomiyama et al.

(10) Patent No.: US 11,023,844 B2
(45) Date of Patent: Jun. 1, 2021

(54) FLIGHT ATTENDANT EVALUATION SYSTEM AND FLIGHT ATTENDANT EVALUATION METHOD

(71) Applicant: PANASONIC INTELLECTUAL PROPERTY MANAGEMENT CO., LTD., Osaka (JP)

(72) Inventors: Naomi Tomiyama, Kyoto (JP); Yasuko Iketsuki, Tokyo (JP); Atsushi Saso, Kanagawa (JP); Takamichi Matsusako, Tokyo (JP); Yuichi Aoki, Osaka (JP); Motoji Ohmori, Osaka (JP); Akira Asai, Osaka (JP)

(73) Assignee: PANASONIC INTELLECTUAL PROPERTY MANAGEMENT CO., LTD., Osaka (JP)

(*) Notice: Subject to any disclaimer, the term of this patent is extended or adjusted under 35 U.S.C. 154(b) by 0 days.

(21) Appl. No.: 16/813,913

(22) Filed: Mar. 10, 2020

(65) Prior Publication Data

US 2020/0210928 A1    Jul. 2, 2020

Related U.S. Application Data

(63) Continuation of application No. 15/800,077, filed on Nov. 1, 2017, now Pat. No. 10,628,773.

(30) Foreign Application Priority Data

Nov. 22, 2016 (JP) .............................. JP2016-226694

(51) Int. Cl.
   *G06Q 10/06* (2012.01)
   *G06Q 50/30* (2012.01)

(52) U.S. Cl.
   CPC ....... *G06Q 10/06398* (2013.01); *G06Q 50/30* (2013.01)

(58) Field of Classification Search
   CPC ..................................................... G06Q 10/06
   See application file for complete search history.

(56) References Cited

U.S. PATENT DOCUMENTS 9,031,857 B2    5/2015 Angell
2014/0106333 A1*  4/2014 Dugan ................ G07C 5/0825
                                                    434/428

(Continued)

FOREIGN PATENT DOCUMENTS

JP    2001/093746    12/2001
JP    2005-148038     6/2005

(Continued)

*Primary Examiner* — Kurtis Gills
(74) *Attorney, Agent, or Firm* — Greenblum & Bernstein, P.L.C.

(57) ABSTRACT

A system includes a biological sensor measuring biological data of a plurality of customers, a storage storing a plurality of attendant-associated data records, and a processor. Each attendant-associated data record includes the biological data of a customer, a seat identifier, and an attendant identifier associated with each other. The processor calculates at least one stress indicator of at least one customer. Each stress indicator is calculated based on the biological data in one of at least one attendant-associated data record extracted from the plurality of attendant-associated data records and associated with a first attendant identifier. The processor further calculates an evaluation value indicated by the first attendant identifier based on the at least one stress indicator of the at least one customer. The evaluation value is updated based on a registered evaluation value identified by the first attendant identifier stored in the storage, and the calculated stress indicator.

16 Claims, 15 Drawing Sheets

(56) References Cited

U.S. PATENT DOCUMENTS

| | | |
|---|---|---|
| 2015/0061825 A1 | 3/2015 | Suzuki et al. |
| 2015/0271329 A1 | 9/2015 | Deshmukh |
| 2016/0157776 A1* | 6/2016 | Mestha .............. A61B 5/02438 600/479 |

FOREIGN PATENT DOCUMENTS

| | | |
|---|---|---|
| JP | 2007-151933 | 6/2007 |
| JP | 2012-120206 | 6/2012 |
| JP | 2012-249797 | 12/2012 |
| JP | 2013-039878 | 2/2013 |
| JP | 2013-058069 | 3/2013 |
| JP | 2015-046065 | 3/2015 |
| JP | 2016-101307 | 6/2016 |

* cited by examiner

| FLIGHT NUMBER IDENTIFIER | SEAT IDENTIFIER | BIOLOGICAL DATA |
|---|---|---|
| PAL485 (OCTOBER 1, 2016, AIRPORT A → AIRPORT B) | LINE 3 A | VT11 |
| ... | ... | ... |
| PAL485 (OCTOBER 1, 2016, AIRPORT A → AIRPORT B) | LINE 10 A | VT12 |
| ... | ... | ... |

| FLIGHT NUMBER IDENTIFIER | ATTENDANT IDENTIFIER | SEAT IDENTIFIER |
|---|---|---|
| PAL485 (OCTOBER 1, 2016, AIRPORT A → AIRPORT B) | J01 | LINE 3 A, LINE 3 B, ... |
| PAL485 (OCTOBER 1, 2016, AIRPORT A → AIRPORT B) | J02 | LINE 10 A, LINE 10 B, ... |
| ... | ... | ... |

| FLIGHT NUMBER IDENTIFIER | SEAT IDENTIFIER | ATTENDANT IDENTIFIER | BIOLOGICAL DATA |
|---|---|---|---|
| PAL485 (OCTOBER 1, 2016, AIRPORT A → AIRPORT B) | LINE 3 A | J01 | VT11 |
| PAL485 (OCTOBER 1, 2016, AIRPORT A → AIRPORT B) | LINE 3 B | J01 | VT13 |
| ... | ... | ... | ... |
| PAL485 (OCTOBER 1, 2016, AIRPORT A → AIRPORT B) | LINE 10 A | J02 | VT12 |
| ... | ... | ... | ... |

| ATTENDANT IDENTIFIER | EVALUATION VALUE |
|---|---|
| J01 | EV1 |
| J02 | EV2 |
| ... | ... |

| ATTENDANT IDENTIFIER | SEX | NAME | AGE | DIVISION |
|---|---|---|---|---|
| J01 | FEMALE | ○○ HANAKO | 25 YEARS OLD | DOMESTIC LINE |
| J02 | MALE | ×× TARO | 31 YEARS OLD | INTERNATIONAL LINE |
| ... | ... | ... | ... | ... |

| FLIGHT NUMBER IDENTIFIER | SEAT IDENTIFIER | FIRST BIOLOGICAL DATA |
|---|---|---|
| PAL485 (OCTOBER 1, 2016, AIRPORT A → AIRPORT B) | LINE 3 A | VT11 |
| ... | ... | ... |
| PAL485 (OCTOBER 1, 2016, AIRPORT A → AIRPORT B) | LINE 10 A | VT12 |
| ... | ... | ... |

FIG. 15

| FLIGHT NUMBER IDENTIFIER | SEAT IDENTIFIER | SECOND BIOLOGICAL DATA |
|---|---|---|
| PAL485 (OCTOBER 1, 2016, AIRPORT A → AIRPORT B) | LINE 3 A | VT21 |

| FLIGHT NUMBER IDENTIFIER | SEAT IDENTIFIER | ATTENDANT IDENTIFIER | FIRST BIOLOGICAL DATA | SECOND BIOLOGICAL DATA |
|---|---|---|---|---|
| PAL485 (OCTOBER 1, 2016, AIRPORT A → AIRPORT B) | LINE 3 A | J01 | VT11 | VT21 |
| PAL485 (OCTOBER 1, 2016, AIRPORT A → AIRPORT B) | LINE 3 B | J01 | VT13 | VT23 |
| ... | ... | ... | ... | ... |
| PAL485 (OCTOBER 1, 2016, AIRPORT A → AIRPORT B) | LINE 10 A | J02 | VT12 | VT22 |
| ... | ... | ... | ... | ... |

| FLIGHT NUMBER IDENTIFIER | SEAT IDENTIFIER | CUSTOMER IDENTIFIER |
|---|---|---|
| PAL485 (OCTOBER 1, 2016, AIRPORT A → AIRPORT B) | LINE 3 A | U03 |
| ... | ... | ... |

| CUSTOMER IDENTIFIER | NAME | FREQUENT FLYER POINTS | ATTRIBUTE |
|---|---|---|---|
| U03 | XXX | 3000 | PREMIUM |
| U04 | YYY | 200 | |
| ... | ... | ... | ... |

FLIGHT ATTENDANT EVALUATION SYSTEM AND FLIGHT ATTENDANT EVALUATION METHOD

CROSS-REFERENCE TO RELATED APPLICATIONS

The present application is a continuation of U.S. application Ser. No. 15/800,077, filed Nov. 1, 2017, which claims the benefit of Japanese Application No. 2016-226694, filed Nov. 22, 2016. The contents of each of the above-mentioned documents are expressly incorporated herein by reference in their entireties.

BACKGROUND

1. Technical Field

The present disclosure relates to a technique for evaluating a flight attendant who provides service for a customer in transportation such as an airplane.

2. Description of the Related Art

In recent years, various techniques have been suggested which use vital data of a person to estimate stress to the person. Accordingly, studies of techniques for providing various services for users by using the technique have been progressing. Japanese Unexamined Patent Application Publication No. 2016-101307 discloses a technique for assessing stress to a target person from biological information of the target person who sits on a seat of an airplane.

SUMMARY

One non-limiting and exemplary embodiment provides a technique for evaluating a flight attendant by using biological data of a customer.

In one general aspect, the techniques disclosed here feature a flight attendant evaluation system including: a first biological sensor that measures first biological data of a customer on board transportation; a storage that stores attendant-associated data in which the first biological data, a seat identifier, and an attendant identifier are associated with each other, the seat identifier indicating a seat of the customer on board, the attendant identifier indicating a flight attendant in charge of the seat; an evaluation value calculator that classifies the attendant-associated data by the attendant identifier, calculates a stress indicator of the customer based on the first biological data associated with a first attendant identifier, and calculates an evaluation value of the flight attendant indicated by the first attendant identifier based on the stress indicator; and a display apparatus that presents the evaluation value.

It should be noted that general or specific embodiments may be implemented as an element, a device, an apparatus, a system, an integrated circuit, a method, or any selective combination thereof.

Additional benefits and advantages of the disclosed embodiments will become apparent from the specification and drawings. The benefits and/or advantages may be individually obtained by the various embodiments and features of the specification and drawings, which need not all be provided in order to obtain one or more of such benefits and/or advantages.

BRIEF DESCRIPTION OF THE DRAWINGS

FIG. 3 is a diagram that illustrates one example of a data configuration of a saved biological table that is stored in a biological data storage unit;

FIG. 4 is a diagram that illustrates one example of a data configuration of an assigned seat table;

FIG. 6 is a diagram that illustrates one example of a data configuration of an attendant-associated table;

FIG. 7 is a diagram that illustrates one example of a data configuration of an evaluation table;

FIG. 8 is a diagram that illustrates one example of a data configuration of an attendant table;

FIG. 14 is a diagram that illustrates one example of a data configuration of a first saved biological table in which first saved biological data are registered in the second embodiment of the present disclosure;

FIG. 15 is a diagram that illustrates one example of a data configuration of second saved biological data according to the second embodiment of the present disclosure;

FIG. 16 is a diagram that illustrates one example of a data configuration of an attendant-associated table in which attendant-associated data are registered according to the second embodiment of the present disclosure;

FIG. 20 is a diagram that illustrates one example of a data configuration of a reservation information table that is used in the flight attendant evaluation system according to the third embodiment of the present disclosure; and FIG. 21 is a diagram that illustrates one example of a data configuration of a customer table that is used in the flight attendant evaluation system according to the third embodiment of the present disclosure.

Figure 1:
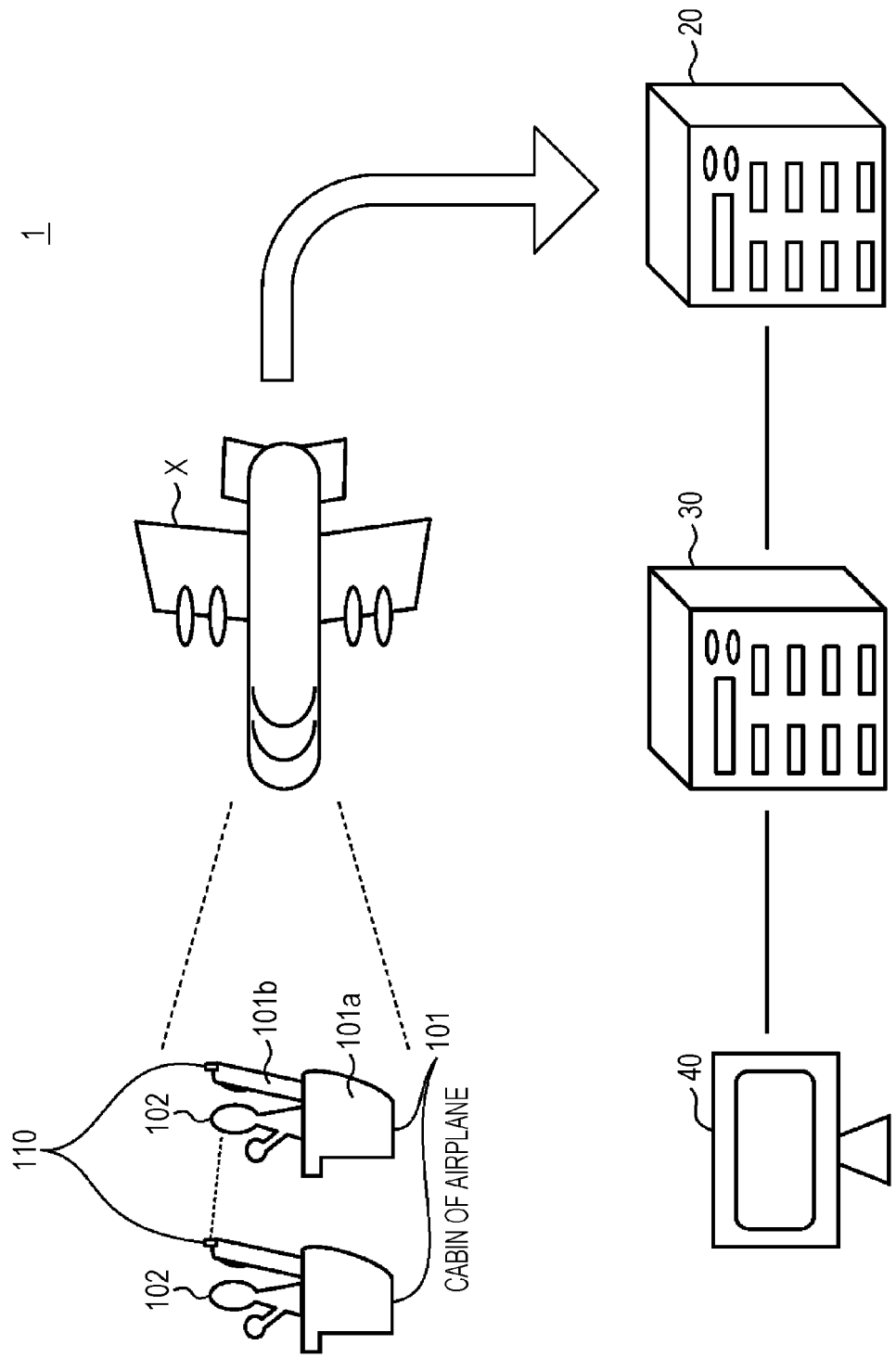
FIG. 1 is a diagram that illustrates one example of a general configuration of a flight attendant evaluation system according to a first embodiment of the present disclosure.

DETAILED DESCRIPTION (Underlying Knowledge Forming Basis of the Present Disclosure)

Above Japanese Unexamined Patent Application Publication No. 2016-101307 discloses a technique of detecting biological information of a target person who sits on a seat by a pressure sensing tube provided to the seat of an airplane, assessing stress of the target person from the detected biological information, and performing a notification to a flight attendant, a pilot, or the like in a case where the assessed stress is high.

However, a fundamental purpose of Japanese Unexamined Patent Application Publication No. 2016-101307 is to provide a biological information acquisition apparatus that may improve detection accuracy of the biological information of the target person (paragraph [0008]). Japanese Unexamined Patent Application Publication No. 2016-101307 only discloses a specific example in which the biological information acquisition apparatus is arranged in a seat portion of an airplane, as one aspect. Further, Japanese Unexamined Patent Application Publication No. 2016-101307 only discloses that a flight attendant or a pilot provides a service with full attention for a target person with high stress, as an effect of the specific example.

Accordingly, Japanese Unexamined Patent Application Publication No. 2016-101307 has a problem in that the flight attendant may not be evaluated based on the stress to the target person.

Incidentally, in a passenger plane, it is typical that an area which a flight attendant himself/herself is in charge of is in advance assigned to each of plural flight attendants and the flight attendant provides service for customers who sit on the seats in the area on board.

Accordingly, in a case where stress indicators of the customers are totaled in each of the areas which is assigned to each of the flight attendants, whether or not the service for the customers by each of the flight attendants is appropriate may be recognized, and as a result each of the flight attendants may be evaluated.

It is desirable to provide a technique for evaluating each of the flight attendants by using biological data of a customer.

A flight attendant evaluation system according to one aspect of the present disclosure includes:

a first biological sensor that measures first biological data of a customer on board transportation;

a storage that stores attendant-associated data in which the first biological data, a seat identifier, and an attendant identifier are associated with each other, the seat identifier indicating a seat of the customer on board, the attendant identifier indicating a flight attendant in charge of the seat;

an evaluation value calculator that classifies the attendant-associated data by the attendant identifier, calculates a stress indicator of the customer based on the first biological data associated with a first attendant identifier, and calculates an evaluation value of the flight attendant indicated by the first attendant identifier based on the stress indicator; and a display apparatus that presents the evaluation value.

In this aspect, the attendant-associated data are stored in which the first biological data of the customer who is boarded on the airplane, the seat identifier which indicates the seat on which the customer sits on board, and the attendant identifier which indicates the flight attendant who is in charge of the seat are associated with each other. Then, the stored attendant-associated data are classified for each of the attendant identifiers, the stress indicators of the customers who on board sit on the seats which each of the flight attendants is in charge of are calculated from the classified attendant-associated data, and the evaluation value of each of the flight attendants is calculated from the calculated stress indicators. Thus, the stress indicators of the customers who each of the flight attendants is in charge of are totaled based on the first biological data, the evaluation value of each of the flight attendants may be calculated in such a manner that the service by the concerned flight attendant is inappropriate in a case where the totaled stress indicator is high and the service by the concerned flight attendant is appropriate in a case where the totaled stress indicator is low, and each of the flight attendants may thereby be evaluated. Then, an evaluation result is presented, customer satisfaction with the service by the flight attendant may thereby be fed back to the flight attendant, and an improvement in the service by the flight attendant may be intended.

In the above aspect, the evaluation value calculator may calculate an average value of stress indicators of customers calculated based on the first biological data associated with the first attendant identifier as the evaluation value of the flight attendant.

In this aspect, because the average value of the stress indicators of the customers is calculated as the evaluation value of each of the flight attendants, the evaluation value of each of the flight attendants may accurately be calculated.

In the above aspect, the display apparatus may present the evaluation value of the flight attendant in a case where an output instruction for evaluation of the flight attendant is detected.

In this aspect, for example, the evaluation value of the desired flight attendant may easily be perceived.

In the above aspect, the evaluation value calculator may perform correction that adds a greater offset value to the stress indicator as the stress indicator is greater in a case where the stress indicator of the customer satisfying a predetermined condition is greater than a first threshold value, and may calculate the evaluation value of the flight attendant based on the corrected stress indicator.

This aspect may lower the evaluation of the flight attendant who performs the service which raises the stress of a highly important second customer such as the customer who uses a special seat (for example, first class or business class) or the customer whose frequent flyer points are high.

In the above aspect, the evaluation value calculator may perform correction that subtracts a greater offset value from the stress indicator as the stress indicator is smaller in a case where the stress indicator of the customer satisfying a predetermined condition is smaller than a second threshold value, and may calculate the evaluation value of the flight attendant based on the corrected stress indicator.

This aspect may raise the evaluation of the flight attendant who performs the service which lowers the stress of the highly important second customer such as the customer who uses the special seat (for example, first class or business class) or the customer whose frequent flyer points are high.

In the above aspect, the flight attendant evaluation system may further include a second biological sensor that measures second biological data of the customer at a time before boarding on the transportation, the storage may store the second biological data associated with the first biological data as the attendant-associated data, and the evaluation value calculator may calculate the stress indicator based on a difference between a first stress indicator and a second stress indicator, the first stress indicator being calculated based on the first biological data, the second stress indicator being calculated based on the second biological data.

In this aspect, the stress indicator is calculated based on the difference between the second stress indicator calculated from the second biological data at a time before the customer boards the airplane, for example, at a time when the customer passes through a boarding gate and the first stress indicator calculated from the first biological data of the customer who has boarded the airplane. Thus, the stress indicator of each of the customers may accurately be calculated.

First Embodiment

FIG. 1 is a diagram that illustrates one example of a general configuration of a flight attendant evaluation system 1 according to a first embodiment of the present disclosure. The flight attendant evaluation system 1 includes plural biological sensors 110 that are mounted on plural seats 101 of an airplane X, a recording apparatus 20 that records the biological data which are measured by the biological sensor 110, a statistical processing apparatus 30 that performs a statistical process of the biological data which are recorded in the recording apparatus 20, and an evaluation display apparatus 40 that displays an evaluation value which is calculated by the statistical processing apparatus 30.

The airplane X is a passenger plane that is owned by an airline company, for example. The airplane X includes the plural seats 101 on which plural customers 102 sit. The biological sensors 110 are respectively provided to the plural seats 101. However, this is one example, and in a case where the biological sensor 110 is configured with a biological sensor that is capable of simultaneously measuring biological data of plural persons, one biological sensor 110 may be provided for plural seats that correspond to plural persons whose biological data are measurable.

The seat 101 includes a seat portion 101a that supports a lumbus of the customer 102 and a back portion 101b that supports a back of the customer 102. The biological sensor 110 is configured with a millimeter-wave radar, for example, and is arranged to be opposed to the customer 102 who sits on the rear seat 101 in the back portion 101b. In the example of FIG. 1, the biological sensor 110 is arranged at an upper end of the back portion 101b. However, this is one example, and the biological sensor 110 may be arranged at the back portion 101b to be positioned in front of a face of the customer 102. The directivity of the biological sensor 110 is set such that a millimeter wave (measurement wave) radiated to the customer is radiated to the vicinity of the face of the sitting customer 102.

Further, in the example of FIG. 1, the biological sensor 110 is provided to the back portion 101b. However, this is one example, and the biological sensor 110 may be provided to a ceiling in a cabin of the airplane X. In this case, the biological sensor 110 may be provided to a ceiling to be positioned directly above each of the seats 101.

The recording apparatus 20 is configured with a computer that includes a CPU, a ROM, a RAM, a communication apparatus, and so forth, for example, and is connected with the airplane X via a predetermined network so as to be capable of communication. The statistical processing apparatus 30 is configured with a computer that includes a CPU, a ROM, a RAM, a communication apparatus, and so forth, for example, and is connected with the recording apparatus 20 via a predetermined network so as to be capable of communication. The evaluation display apparatus 40 is configured with a computer that includes a CPU, a ROM, a RAM, a communication apparatus, and so forth and is connected with the statistical processing apparatus 30 via a predetermined network so as to be capable of communication. The evaluation display apparatus 40 is configured with a stationary computer, for example. However, this is one example, and the evaluation display apparatus 40 may be configured with a portable computer such as a smartphone, a tablet terminal, or a feature phone with buttons.

The evaluation display apparatus 40 may be configured with a computer that is installed in a management department that manages the flight attendants in an airline company or may be configured with a portable computer that is possessed by each of the flight attendants or a manager who manages each of the flight attendants, for example.

Figure 2:
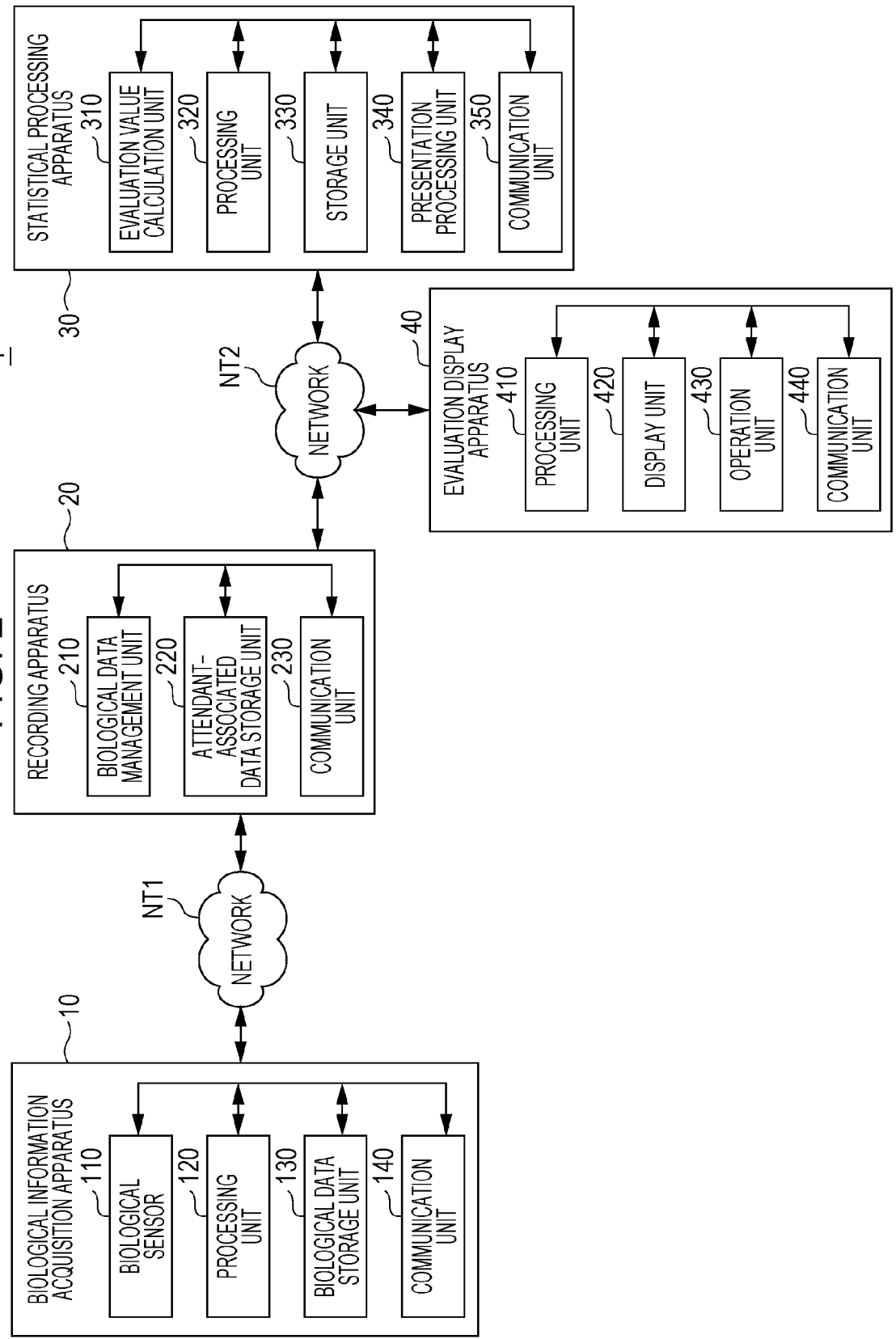
FIG. 2 is a block diagram that illustrates a configuration of the flight attendant evaluation system according to the first embodiment of the present disclosure.

FIG. 2 is a block diagram that illustrates a configuration of the flight attendant evaluation system 1 according to the first embodiment of the present disclosure. The flight attendant evaluation system 1 includes a biological information acquisition apparatus 10 that is provided to the airplane X, the recording apparatus 20, the statistical processing apparatus 30, and the evaluation display apparatus 40 which are illustrated in FIG. 1. The biological information acquisition apparatus 10 and the recording apparatus 20 are connected via a network NT1 so as to be capable of mutual communication. As the network NT1, a public telecommunication network, which includes a radio communication network such as Wi-Fi® which is capable of communication between an airplane and a base station on the ground, may be employed.

The recording apparatus 20, the statistical processing apparatus 30, and the evaluation display apparatus 40 are connected via a network NT2 so as to be capable of mutual communication. As the network NT2, a public telecommunication network, which includes a cellular phone communication network, a Wi-Fi® communication network, an Internet communication network, and so forth, may be employed. Note that for convenience of description, FIG. 2 separately illustrates the network NT1 and the network NT2. However, this is one example, and both of the networks may be the same.

The biological information acquisition apparatus 10 is configured with a computer that is provided in the airplane X, for example, and includes the biological sensor 110 (one example of a first biological sensor), a processing unit 120, a biological data storage unit 130, and a communication unit 140.

The biological sensor 110 is connected with the communication unit 140 so as to be capable of communication by a wireless LAN or a wired LAN, measures biological data of the customer 102 who sits on the seat 101, and transmits the biological data to the communication unit 140. In recent years, a measurement technique has been known which simultaneously and contactlessly measures the biological data of plural persons by using a millimeter-wave radar. Specifically, this measurement technique radiates a millimeter wave of 60 GHz band to a person, for example, extracts a heartbeat signal from a measured radar signal, extracts phase characteristic points from the extracted heartbeat signal, and estimates heartbeat intervals from a time-series pattern of the extracted phase characteristic points.

Then, in a case where the heartbeat intervals may be estimated, a frequency analysis of the fluctuation of the heartbeat intervals is performed as disclosed in Japanese Patent No. 5257525, for example, and the stress to a person may thereby be detected.

Accordingly, in this embodiment, the millimeter-wave radar is employed as the biological sensor 110.

Further, Japanese Unexamined Patent Application Publication No. 2016-101307, which is described in description of the related art, discloses a technique for measuring the biological data of a target person based on a pressure sensing tube attached to the seat portion 101a and the signal that corresponds to an internal pressure which occurs in the pressure sensing tube. Accordingly, in the present disclosure, the biological information of the customer 102 may be measured by using the technique disclosed in Japanese Unexamined Patent Application Publication No. 2016-101307.

The processing unit 120 is configured with a CPU, for example, and conducts general control of the biological information acquisition apparatus 10. The processing unit 120 generates saved biological data by associating the biological data measured by the biological sensor 110 with a seat identifier and with a flight number identifier of the airplane X and stores the saved biological data in the biological data storage unit 130. The biological data storage unit 130 is configured with a non-volatile storage apparatus, for example, and stores a saved biological table T1 in which the saved biological data are registered.

FIG. 3 is a diagram that illustrates one example of a data configuration of the saved biological table T1 that is stored in the biological data storage unit 130. The saved biological table T1 is a table in which one piece of saved biological data is registered in one record and includes fields of "flight number identifier", "seat identifier", and "biological data".

"Flight number identifier" is an identifier of the airplane X and includes a flight number, a flight date, and a flight route. In the example of FIG. 3, the flight number identifier that is configured with the flight number of "PAL485", the flight date of "Oct. 1, 2016", and the flight route of "Airport A to Airport B" is registered.

"Seat identifier" is information that identifies each of plural seats in the cabin of the airplane X and employs a symbol string that is uniquely allocated to each of the seats. In the field of "biological data", the biological data measured by the biological sensor 110 are registered.

Here, because the biological sensor 110 measures the biological data at regular sampling intervals while the airplane X is flying, the biological data become time-series data of measurement values of the biological data by the biological sensor 110. The biological sensor 110 transmits the biological data that are associated with the seat identifier which is in advance allocated to the biological sensor 110. Thus, the processing unit 120 may generate the saved biological data while associating the seat identifier with the biological data. Note that as the seat identifier allocated to the biological sensor 110, as illustrated in FIG. 1, the seat identifier of the seat 101 on which the customer 102 to be a measurement target sits is employed. Note that the processing unit 120 in advance stores the flight number identifier.

FIG. 2 will be referred to. The communication unit 140 is configured with a communication apparatus that connects the biological information acquisition apparatus 10 with the network NT1 by using radio communication such as Wi-Fi®, for example. The communication unit 140 transmits the saved biological data stored in the biological data storage unit 130 to the recording apparatus 20 via the network NT1 under control of the processing unit 120. Here, the communication unit 140 may transmit the saved biological data to the recording apparatus 20 under control of the processing unit 120 when the airplane X arrives at a destination. However, this is one example, and the communication unit 140 may transmit the saved biological data to the recording apparatus 20 at each time when the saved biological data are generated, that is, each time when the biological sensor 110 measures the biological data.

Further, the communication unit 140 acquires the biological data measured by the biological sensor 110 via a wireless LAN or a wired LAN, which is provided in the airplane X.

The recording apparatus 20 includes a biological data management unit 210, an attendant-associated data storage unit 220 (one example of a storage), and a communication unit 230. In FIG. 2, the biological data management unit 210 is configured with a CPU, for example. Further, the attendant-associated data storage unit 220 is configured with a non-volatile storage apparatus, for example. The communication unit 230 is configured with a communication apparatus that connects the recording apparatus 20 with the networks NT1 and NT2, for example.

The biological data management unit 210 generates the attendant-associated data by associating the saved biological data transmitted from the biological information acquisition apparatus 10 with an attendant identifier and stores the attendant-associated data in the attendant-associated data storage unit 220. Here, in a case where the saved biological data are transmitted from the biological information acquisition apparatus 10, the biological data management unit 210 may acquire the attendant identifier that corresponds to the seat identifier and the flight number identifier, which are included in the transmitted saved biological data, by referring to an assigned seat table T2 (FIG. 4).

FIG. 4 is a diagram that illustrates one example of a data configuration of the assigned seat table T2. The assigned seat table T2 is configured with a database in which one piece of assigned seat data is registered in one record and includes fields of "flight number identifier", "attendant identifier", and "seat identifier". The assigned seat data are data that indicate which seats of which airplane flights each of the flight attendants is in charge of.

"Flight number identifier" and "seat identifier" are the same as FIG. 3. "Attendant identifier" is configured with a symbol string that is uniquely allocated in order to distinguish each of the flight attendants. In the example of the assigned seat data in the first row in FIG. 4, for the flight number identifier "PAL485, Oct. 1, 2016, Airport A→Airport B", the flight attendant of the attendant identifier "J01" is in charge of the area that is configured with the seats indicated by the seat identifiers "line 3 A, line 3 B, . . . ".

In such a manner, "flight number identifier", "attendant identifier", and "seat identifier", which are associated with each other, are registered in the assigned seat table T2. Thus, the biological data management unit 210 may specify the associated "attendant identifier" from "flight number identifier" and "seat identifier" included in the saved biological data and may generate the attendant-associated data.

Figure 5:
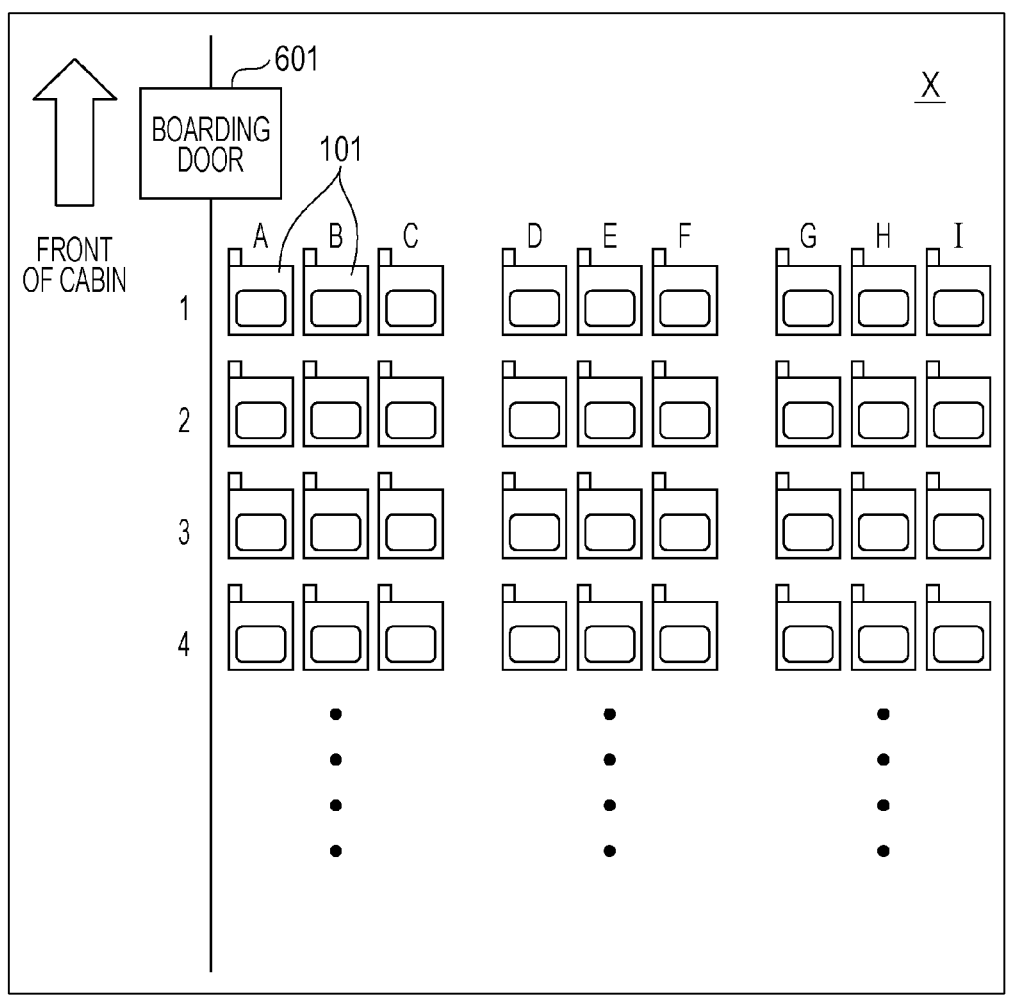
FIG. 5 is a diagram that illustrates one example of a seat arrangement diagram which illustrates arrangement of seats in a cabin of an airplane.

FIG. 5 is a diagram that illustrates one example of a seat arrangement diagram which illustrates arrangement of the seats 101 in the cabin of the airplane X. The arrow in this seat arrangement diagram points towards the front of the cabin. Further, in this seat arrangement diagram, the seat identifier is given to each of the seats 101 by a pair of a value that indicates the order in a line in a transverse direction and a symbol that indicates the order in a line in a longitudinal direction. Values such as "1", "2", and "3" are assigned to the lines in the transverse direction in the order from the front, and symbols such as "A", "B", and "C" are assigned to the lines in the longitudinal direction from the left to the right. In this example, because the nine lines of seats 101 in the longitudinal direction are provided, nine symbols of "A" to "I" are assigned to the lines in the longitudinal direction. Accordingly, the seat 101 that is positioned in the upper left apex has the seat identifier "1A", and the seat 101 that is in the next position on the right has the seat identifier "1B". Note that in FIG. 5, the nine lines of seats 101 in the longitudinal direction are provided. However, this is one example, and 10 or more or 8 or less lines of seats 101 may be provided. A boarding door 601 that communicates with the outside of the airplane X is provided in front of the seat of the seat identifier "1A".

An area of the seats 101 which the flight attendant himself/herself is in charge of is in advance defined for each of the flight attendants, and the flight attendant basically performs service for the customers 102 who sit on the seats 101 in the area. In the example of FIG. 5, such as the area formed with the lines "1" to "4" in the transverse direction and the lines "A" to "C" in the longitudinal direction for the flight attendant of "J01", the area formed with the lines "1" to "4" in the transverse direction and the lines "D" to "F" in the longitudinal direction for the flight attendant of "J02", and the area formed with the lines "1" to "4" in the transverse direction and the lines "G" to "H" in the longitudinal direction for the flight attendant of "J03", the area which the flight attendant himself/herself is in charge of is in advance defined for each of the flight attendants. Accordingly, in a case where the stress indicator of the customer 102 who sits on the seat 101 in a certain area is high, it may be considered that the service by the flight attendant who is in charge of the area is inappropriate. On the other hand, in a case where the stress indicator of the customer 102 who sits on the seat 101 in the area which the flight attendant is in charge of is low, it may be considered that the service by the flight attendant who is in charge of that area is appropriate. This embodiment focuses on this point and evaluates the service for the customers 102 by each of the flight attendants.

FIG. 2 will be referred to again. The attendant-associated data storage unit 220 stores an attendant-associated table T3 in which the attendant-associated data are registered. FIG. 6 is a diagram that illustrates one example of a data configuration of the attendant-associated table T3. The attendant-associated table T3 is a database in which one piece of attendant-associated data is registered in one record and includes fields of "flight number identifier", "seat identifier", "attendant identifier", and "biological data". The attendant-associated data are data in which "attendant identifier" is further associated with the saved biological data illustrated in FIG. 3. "Flight number identifier" and "seat identifier" are the same as FIG. 3. In the field of "biological data", the biological data of each of the customers 102 are registered. "Attendant identifier" is the same as "attendant identifier" indicated in FIG. 4.

In FIG. 6, with respect to the attendant identifier "J01", biological data VT11 are registered as "biological data" of the customer 102 of the seat identifier "line 3 A", and biological data VT13 are registered as "biological data" of the customer 102 of the seat identifier "line 3 B". Further, with respect to the attendant identifier "J02", biological data VT12 are registered as "biological data" of the customer 102 of the seat identifier "line 10 A". However, this is one example. Actually, the attendant-associated data about all the seats, which all the flight attendants to be management targets are in charge of, are registered in the attendant-associated table T3.

In such a manner, because the biological data of the customers whom each of the flight attendants is in charge of are registered in the attendant-associated table T3, an evaluation value calculation unit 310 that will be described later may calculate the evaluation value of each of the flight attendants.

FIG. 2 will be referred to again. The communication unit 230 transmits the attendant-associated data registered in the attendant-associated table T3 to the statistical processing apparatus 30 via the network NT2 under control of the biological data management unit 210.

Here, the communication unit 230 may transmit the attendant-associated data to the statistical processing apparatus 30 at each time when the number of pieces of attendant-associated data registered in the attendant-associated table T3 increases by a certain number, or the communication unit 230 may transmit the attendant-associated data to the statistical processing apparatus 30 at each time when a certain time elapses (for example, by one day). In this case, the communication unit 230 may not transmit the attendant-associated data that are already transmitted. Further, the communication unit 230 may delete the attendant-associated data that are already transmitted from the attendant-associated table T3. Further, in a case where the saved biological data are transmitted from the biological information acquisition apparatus 10 to the recording apparatus 20 at each time when the biological data are measured, the communication unit 230 may transmit the attendant-associated data to the statistical processing apparatus 30 at each time when new attendant-associated data are registered in the attendant-associated table T3.

The statistical processing apparatus 30 includes the evaluation value calculation unit 310, a processing unit 320, a storage unit 330, a presentation processing unit 340, and a communication unit 350. In FIG. 2, the evaluation value calculation unit 310, the processing unit 320, and the presentation processing unit 340 are configured with CPUs, for example, and the storage unit 330 is configured with a non-volatile storage apparatus, for example. The communication unit 350 is configured with a communication apparatus for connecting the statistical processing apparatus 30 with the network NT2.

In a case where the communication unit 350 receives the attendant-associated data transmitted from the recording apparatus 20, the processing unit 320 causes the storage unit 330 to store the received attendant-associated data. Specifically, similarly to the attendant-associated data storage unit 220, the storage unit 330 stores the attendant-associated table T3 (FIG. 6) in which the attendant-associated data which is transmitted from the recording apparatus 20 are registered. Accordingly, the processing unit 320 registers the attendant-associated data transmitted from the recording apparatus 20 in the attendant-associated table T3.

The evaluation value calculation unit 310 classifies the attendant-associated data that are registered in the attendant-associated table T3 stored in the storage unit 330 for each of the attendant identifiers, calculates the stress indicators of the customers 102 who sit on the seats 101 which each of the flight attendants is in charge of from the biological data included in the classified attendant-associated data, and calculates the evaluation value of each of the flight attendants from the calculated stress indicators.

In this embodiment, the millimeter-wave radar is employed as the biological sensor 110. Accordingly, the evaluation value calculation unit 310 estimates the heartbeat intervals from the biological data measured by the biological sensor 110, performs the frequency analysis of the fluctuation of the heartbeat intervals, which is disclosed in above-described Japanese Patent No. 5257525, for the estimated heartbeat intervals, and may thereby calculate the stress indicator (the stress indicator for each piece of attendant-associated data) of the customer 102 who on board sits on the seat 101 which each of the flight attendants is in charge of.

Specifically, the evaluation value calculation unit 310 performs the frequency analysis of the estimated heartbeat intervals, thereby detects a level HF of a high-frequency peak that occurs around a frequency of 0.3 Hz and a level LF of a low-frequency peak that occurs around 0.1 Hz, and may thereby calculate LF/HF as the stress indicator. Note that the value of LF/HF increases as the stress becomes higher. Accordingly, the higher value of the stress indicator indicates the higher stress.

Then, the evaluation value calculation unit 310 classifies the stress indicators calculated for each piece of the attendant-associated data for each of the flight attendants and calculates the average value of the stress indicators for each of the flight attendants as the evaluation value of each of the flight attendants. In the example of FIG. 6, with respect to the flight attendant of the attendant identifier "J01", for example, the average value of the stress indicator that is obtained from the biological data VT11 and the stress indicator that is obtained from the biological data VT13 is calculated as the evaluation value.

The evaluation value calculation unit 310 registers the evaluation value that is calculated for each of the flight attendants in an evaluation table T4 that is stored in the storage unit 330. FIG. 7 is a diagram that illustrates one example of a data configuration of the evaluation table T4. The evaluation table T4 is configured with a database in which one flight attendant is assigned to one record and includes fields of "attendant identifier" and "evaluation value". "Attendant identifier" is the same as FIG. 4. "Evaluation value" is a value for evaluating each of the flight attendants. In such a manner, because the evaluation value of each of the flight attendants is registered in the evaluation table T4, the evaluation display apparatus 40 that will be described later may display the evaluation value of each of the flight attendants.

Note that in the attendant-associated table T3 stored in the storage unit 330, the evaluation value calculation unit 310 may not calculate the stress indicators for the attendant-associated data for which the stress indicators are already calculated. In this case, the evaluation value calculation unit 310 may calculate the stress indicators only for the attendant-associated data that are newly added to the attendant-associated table T3. Then, the evaluation value calculation unit 310 classifies the calculated stress indicators for each of the flight attendants, calculates the evaluation value of each of the flight attendants from the classified stress indicators, calculates the average value of the calculated evaluation value and the evaluation value that is already registered in the evaluation table T4, and may thereby newly calculate the evaluation value for each of the flight attendants. Then, the evaluation value calculation unit 310 updates the evaluation table T4 with the newly calculated evaluation value for each of the flight attendants.

The storage unit 330 stores the attendant-associated table T3 (FIG. 6), the evaluation table T4 (FIG. 7), and an attendant table T5 (FIG. 8). FIG. 8 is a diagram that illustrates one example of a data configuration of the attendant table. The attendant table T5 is a database in which personal data of one flight attendant is assigned to one record and includes fields of "attendant identifier", "sex", "name", "age", and "division".

"Attendant identifier" is the same as FIG. 4. The sex, name, and age of the concerned flight attendant are respectively registered in the fields of "sex", "name", and "age". The air route or department which the concerned flight attendant works for or belongs to in an airline company is registered in the field of "division". Here, "domestic line" and "international line" are registered as "division". However, this is one example.

In a case where the communication unit 350 receives an inquiry signal for inquiring the evaluation value of a certain flight attendant, the presentation processing unit 340 extracts the evaluation value of the flight attendant who is designated by the inquiry signal from the evaluation table T4. The presentation processing unit 340 transmits the extracted evaluation value to the evaluation display apparatus 40 by using the communication unit 350 and causes the evaluation display apparatus 40 to present the evaluation value. In this case, the presentation processing unit 340 may read out the personal data of the concerned flight attendant from the attendant table T5, combine the personal data that are read out with the evaluation value, transmit the personal data and the evaluation value to the evaluation display apparatus 40 by using the communication unit 350, and thereby cause the evaluation display apparatus 40 to present the personal data.

The communication unit 350 receives the attendant-associated data transmitted from the recording apparatus 20 via the network NT2 under control of the processing unit 320. Further, the communication unit 350 receives the inquiry signal for the evaluation value from the evaluation display apparatus 40.

The evaluation display apparatus 40 includes a processing unit 410, a display unit 420, an operation unit 430, and a communication unit 440. In FIG. 2, the processing unit 410 is configured with a CPU, for example. The display unit 420 is configured with a display apparatus such as a liquid crystal panel. The operation unit 430 is configured with input apparatuses such as a touch panel, a keyboard, and a mouse. The communication unit 440 is configured with a communication apparatus for connecting the evaluation display apparatus 40 with the network NT2.

In a case where the operation unit 430 receives an output instruction for the evaluation value of any flight attendant among the flight attendants, the processing unit 410 transmits the output instruction to the statistical processing apparatus 30 by using the communication unit 440. Further, in a case where the evaluation value is transmitted from the recording apparatus 20, the processing unit 410 causes the display unit 420 to display an evaluation image (FIG. 9) that indicates the evaluation value.

The display unit 420 displays various kinds of images (such as the evaluation image) under control of the processing unit 410. The operation unit 430 receives various kinds of operations (such as the output instruction for the evaluation value) from an operator. Here, the operation unit 430 causes the name or the attendant identifier of the flight attendant, evaluation value of which is desired to be output, to be input in a name input section and/or an identifier input section that are provided to an input image (not illustrated) displayed on the display unit 420 and thereby receives the output instruction. The processing unit 410 generates the inquiry signal for the evaluation value that includes the name and/or the attendant identifier of the flight attendant who is designated by the received output instruction and transmits the inquiry signal to the evaluation display apparatus 40 by using the communication unit 440.

The communication unit 440 receives various kinds of information (such as the evaluation value) from the statistical processing apparatus 30 and transmits various kinds of information (such as the inquiry signal for the evaluation value) to the statistical processing apparatus 30.

Figure 9:
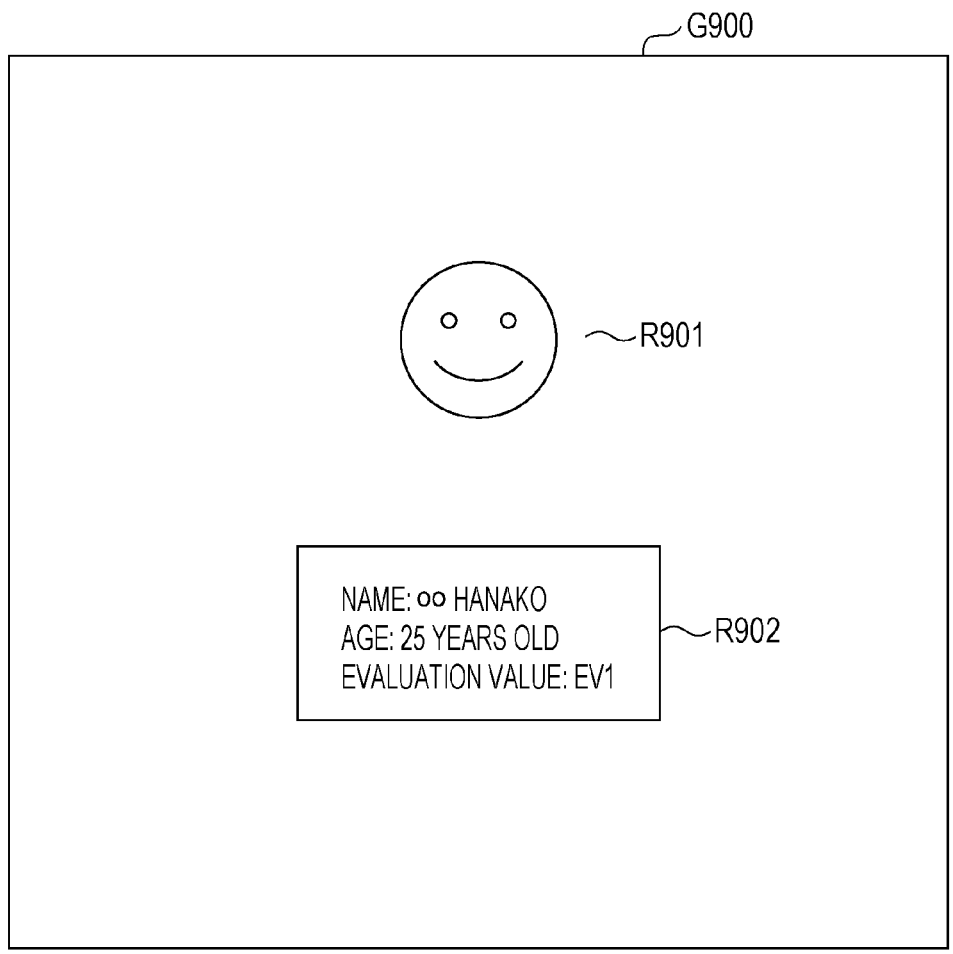
FIG. 9 is a diagram that illustrates one example of an evaluation image that is displayed by an evaluation display apparatus.

FIG. 9 is a diagram that illustrates one example of an evaluation image G900 that is displayed by the evaluation display apparatus 40. The evaluation image G900 includes a face image display section R901 that displays a face image of the concerned flight attendant and a personal data display section R902 that displays the personal data of the concerned flight attendant. The personal data display section R902 includes "name", "age", and "evaluation value" of the concerned flight attendant. Note that "name", "age", and the face image of the concerned flight attendant are transmitted together with the evaluation value of the concerned flight attendant from the statistical processing apparatus 30.

Figure 10:
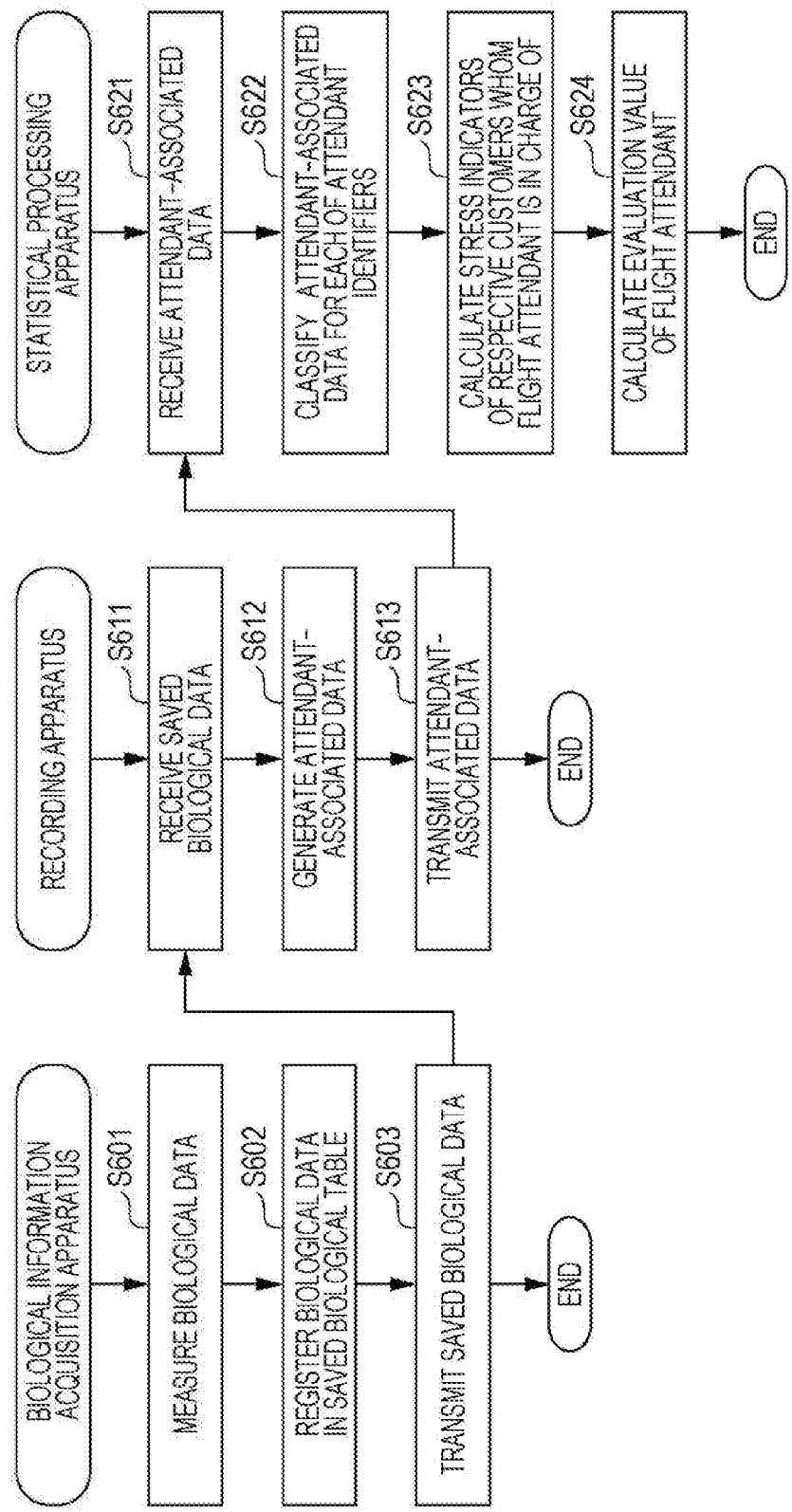
FIG. 10 is a flowchart that illustrates one example of a process from measurement of biological data to calculation of an evaluation value in the flight attendant evaluation system according to the first embodiment of the present disclosure.

FIG. 10 is a flowchart that illustrates one example of a process from measurement of the biological data to calculation of the evaluation value in the flight attendant evaluation system 1 according to the first embodiment of the present disclosure.

First, the biological sensor 110 of the biological information acquisition apparatus 10 measures the biological data (S601). Here, the biological sensor 110 measures the biological data at predetermined sampling intervals.

Next, the processing unit 120 of the biological information acquisition apparatus 10 registers the measured biological data in the saved biological table T1 (S602). Specifically, the processing unit 120 generates the saved biological data by associating the measured biological data with the seat identifier and with the flight number identifier, and stores the saved biological data in the saved biological table T1.

Next, the communication unit 140 of the biological information acquisition apparatus 10 transmits all the saved biological data registered in the saved biological table T1 to the recording apparatus 20 when the airplane X arrives at a destination (S603). Note that in a case where the transmission of the saved biological data to the recording apparatus 20 finishes, the processing unit 120 may delete the saved biological data that are registered in the saved biological table T1. Further, in a case where the saved biological data are transmitted to the recording apparatus 20 at each time when the saved biological data are generated, the saved biological table T1 is not requested.

Next, the communication unit 230 of the recording apparatus 20 receives the saved biological data from the biological information acquisition apparatus 10 (S611). Next, the biological data management unit 210 of the recording apparatus 20 extracts the attendant identifier that corresponds to the flight number identifier and the seat identifier, which are included in the received saved biological data, by referring to the assigned seat table T2. The biological data management unit 210 associates the extracted attendant identifier with the saved biological data, generates the attendant-associated data, and registers the attendant-associated data in the attendant-associated table T3 (S612).

Next, the communication unit 230 of the recording apparatus 20 transmits the attendant-associated data registered in the attendant-associated table T3 to the statistical processing apparatus 30 under control of the biological data management unit 210 (S613). In this case, as described above, the communication unit 230 may transmit the attendant-associated data to the statistical processing apparatus 30 at each time when the number of pieces of attendant-associated data registered in the attendant-associated table T3 increases by a certain number or at each time when a certain time elapses, for example.

Next, the communication unit 350 of the statistical processing apparatus 30 receives the attendant-associated data transmitted from the recording apparatus 20 (S621). In this case, the processing unit 320 registers the received attendant-associated data in the attendant-associated table T3 stored in the storage unit 330.

Next, the evaluation value calculation unit 310 of the statistical processing apparatus 30 classifies the attendant-associated data registered in the attendant-associated table T3 for each of the attendant identifiers (S622).

In the example of FIG. 6, because the attendant-associated data of the flight attendants of the attendant identifier "J01" and the attendant identifier "J02" are registered, the attendant-associated data are classified for each of both flight attendants.

Next, the evaluation value calculation unit 310 calculates the stress indicators of the customers 102 who on board sit on the seats 101 which each of the flight attendants is in charge of from the biological data included in the classified attendant-associated data (S623). In the example of FIG. 6, with respect to the flight attendant of the attendant identifier "J01", the stress indicator that corresponds to the biological data VT11 is calculated, and the stress indicator that corresponds to the biological data VT13 is calculated. Further, in the example of FIG. 6, with respect to the flight attendant of the attendant identifier "J02", the stress indicator that corresponds to the biological data VT12 is calculated.

Next, the evaluation value calculation unit 310 calculates the average of the calculated stress indicators for each of the flight attendants as the evaluation value of each of the flight attendants (S624) and registers the evaluation value in the evaluation table T4.

As a result, the stress indicators are calculated from the biological data of the customers 102 whom each of the flight attendants is in charge of, and the evaluation value of each of the flight attendants is calculated from the calculated stress indicators.

Figure 11:
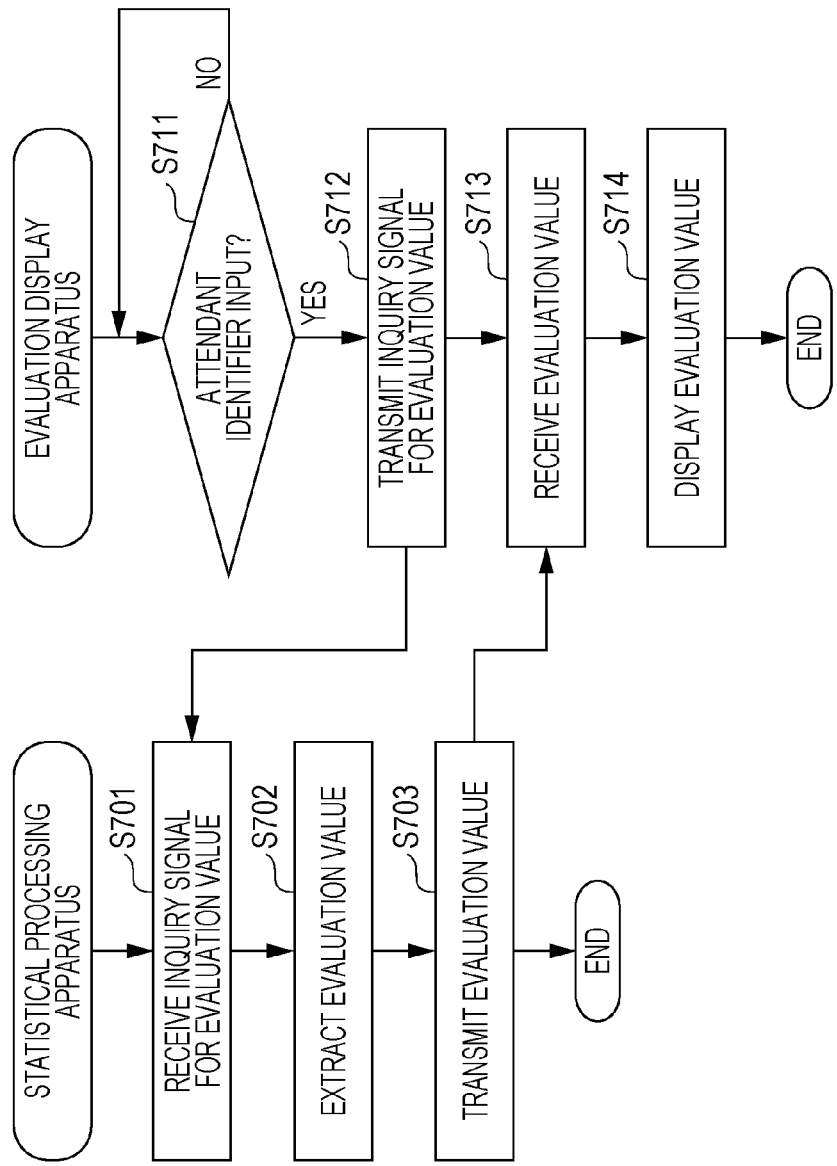
FIG. 11 is a flowchart that illustrates one example of a process of presenting the evaluation value in the flight attendant evaluation system according to the first embodiment of the present disclosure.

FIG. 11 is a flowchart that illustrates one example of a process of presenting the evaluation value in the flight attendant evaluation system 1 according to the first embodiment of the present disclosure.

First, the operation unit 430 of the evaluation display apparatus 40 receives an input of the output instruction of the evaluation value of any of the flight attendants (S711). In a case where the input of the output instruction is received (YES in S711), the communication unit 440 of the evaluation display apparatus 40 transmits the inquiry signal for the evaluation value that includes the name and/or the attendant identifier of the flight attendant who is designated by the output instruction to the statistical processing apparatus 30 (S712).

On the other hand, in a case where the input of the output instruction is not received (NO in S711), the process is returned to S711.

Next, the communication unit 350 of the statistical processing apparatus 30 receives the inquiry signal for the evaluation value (S701). Next, the presentation processing unit 340 extracts the evaluation value of the concerned flight attendant from the evaluation table T4 (S702). Next, the communication unit 350 of the statistical processing apparatus 30 transmits the extracted evaluation value that is combined with the personal data of the concerned flight attendant to the evaluation display apparatus 40 (S703).

Next, the communication unit 440 of the evaluation display apparatus 40 receives the evaluation value and the personal data (S713). Next, the processing unit 410 of the evaluation display apparatus 40 generates the evaluation image G900 from the received evaluation value and personal data and causes the display unit 420 to display the evaluation image G900 (S714). Accordingly, the evaluation image G900 illustrated in FIG. 9 is presented.

In such a manner, in the flight attendant evaluation system 1, the attendant-associated data are stored in which the biological data of the customers 102 who are boarded on the airplane X, the seat identifiers which indicate the seats 101 on which the customers 102 sit, and the attendant identifier which indicates the flight attendant who is in charge of the seats 101 are associated with each other. Then, the stored attendant-associated data are classified for each of the attendant identifiers, and the stress indicators of the customers 102 who on board sit on the seats 101 which each of the flight attendants is in charge of are calculated from the classified attendant-associated data. Then, the evaluation value of each of the flight attendants is calculated from the calculated stress indicators. Thus, the stress indicators of the customers whom each of the flight attendants is in charge of are totaled based on the biological data, and the evaluation value of each of the flight attendants may be calculated in such a manner that the service by the concerned flight attendant is inappropriate in a case where the totaled stress indicator is high and the service by the concerned flight attendant is appropriate in a case where the totaled stress indicator is low. Then, an evaluation result is presented, customer satisfaction with the service by the flight attendant may thereby be fed back to the flight attendant, and an improvement in the service by the flight attendant may be intended.

Second Embodiment

Figure 12:
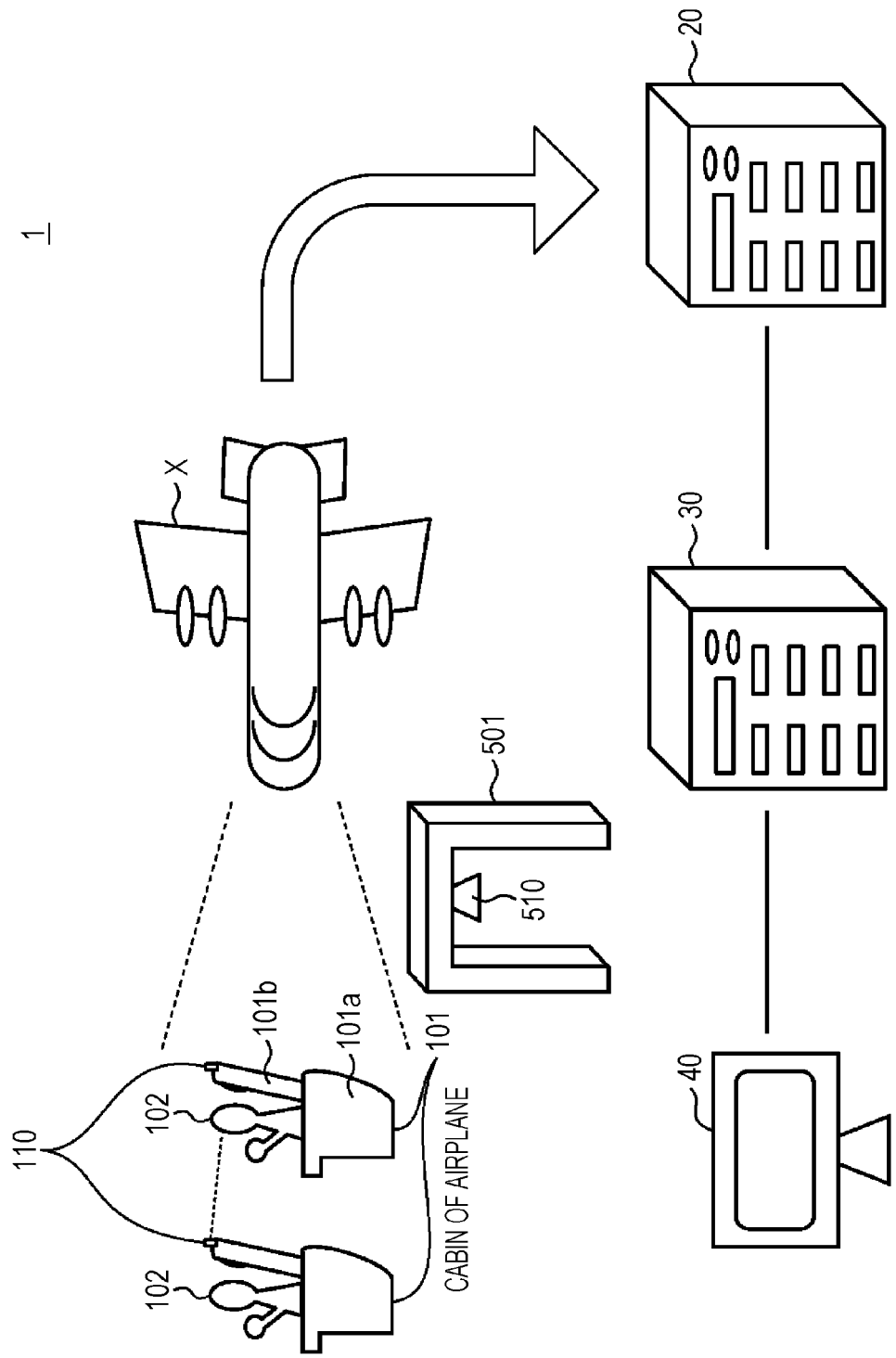
FIG. 12 is a diagram that illustrates one example of a general configuration of a flight attendant evaluation system according to a second embodiment of the present disclosure.

FIG. 12 is a diagram that illustrates one example of a general configuration of a flight attendant evaluation system 1A according to a second embodiment of the present disclosure. In addition to the measurement of the biological data in the airplane X, the flight attendant evaluation system 1A has a characteristic that the biological data are measured by using a biological sensor 510 (one example of a second biological sensor) that is provided to a boarding gate 501 in an airport and the stress indicator is calculated by using both pieces of the biological data. Note that in the second embodiment, the same reference characters will be given to the same configuration elements as the first embodiment, and a description will not be made.

The boarding gate 501 is a gate through which the customer 102 passes immediately before boarding the airplane X.

The biological sensor 510 is used for measuring the stress of the customer 102 in a state where the customer 102 does not board the airplane X. In a case where the customer 102 boards the airplane X of a domestic line in the airport, for example, it is typical to follow the procedures in which the customer 102 first performs boarding procedures at a check-in counter, next leaves a large baggage at a baggage counter, next goes through a security check at an inspection area, and finally passes through the boarding gate. It is sufficient that the biological sensor 510 may measure the biological data of the customer 102 at a time before boarding the airplane X. Thus, the installation place of the biological sensor 510 is not limited to the boarding gate 501 but may be the check-in counter, the baggage counter, or the inspection area.

Figure 13:
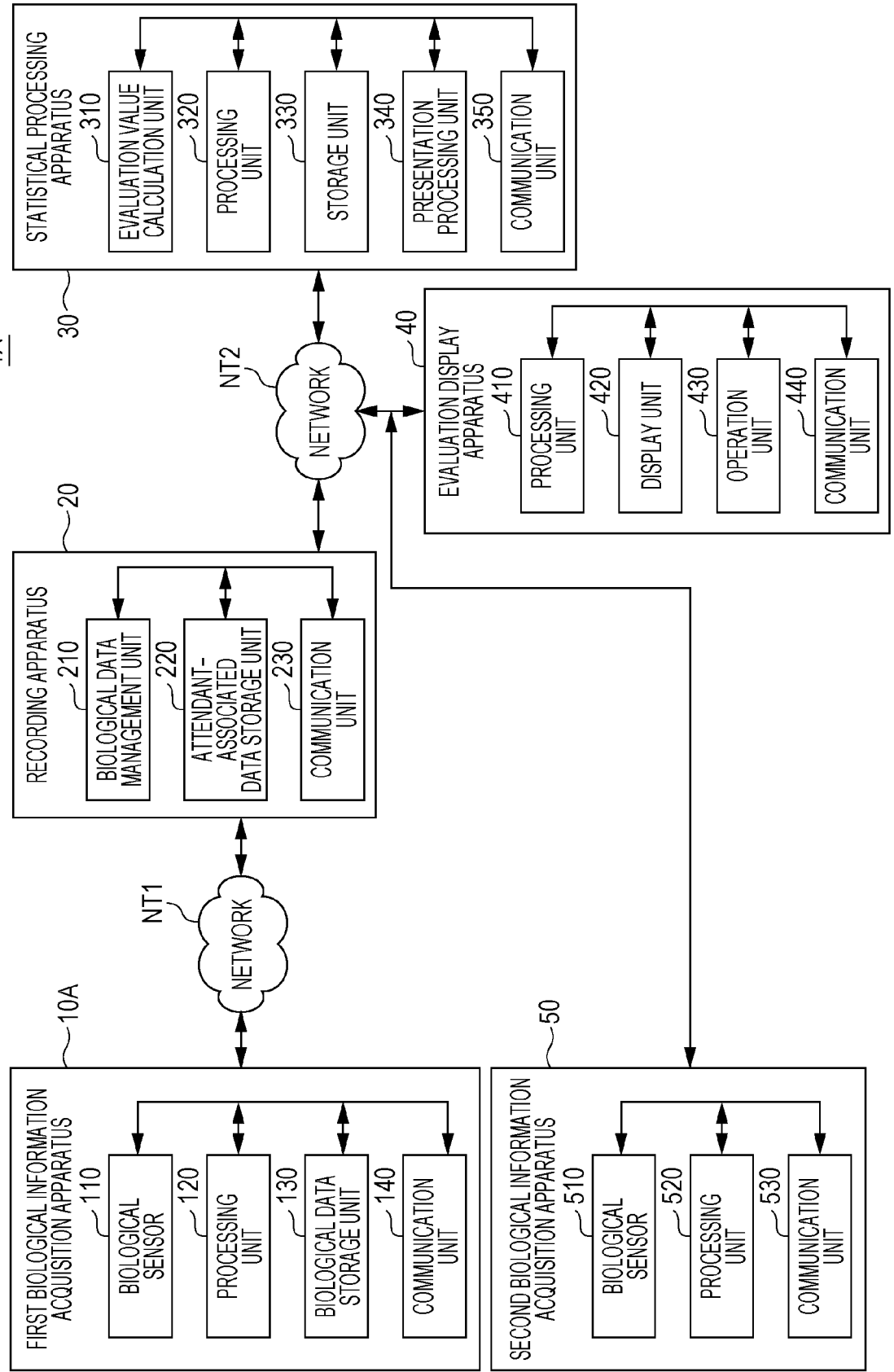
FIG. 13 is a block diagram that illustrates a configuration of the flight attendant evaluation system according to the second embodiment of the present disclosure.

FIG. 13 is a block diagram that illustrates a configuration of the flight attendant evaluation system 1A according to the second embodiment of the present disclosure. The flight attendant evaluation system 1A is further provided with a second biological information acquisition apparatus 50 compared to the flight attendant evaluation system 1 illustrated in FIG. 2. Note that in the second embodiment, in order to distinguish the biological information acquisition apparatus 10 of the first embodiment from the second biological information acquisition apparatus 50, the biological information acquisition apparatus 10 will be referred to as a first biological information acquisition apparatus 10A. Further, in the second embodiment, in order to distinguish the biological data that are measured by the biological sensor 510 from the biological data that are measured by the biological sensor 110, the biological data measured by the biological sensor 510 will be referred to as second biological data, and the biological data measured by the biological sensor 110 will be referred to as the first biological data.

The second biological information acquisition apparatus 50 includes the biological sensor 510, a processing unit 520, and a communication unit 530. The biological sensor 510 employs the millimeter-wave radar, for example, similarly to the biological sensor 110.

The processing unit 520 is configured with a CPU, for example, and conducts general control of the second biological information acquisition apparatus 50. The processing unit 520 associates the second biological data measured by the biological sensor 510 with the seat identifier and with the flight number identifier, and transmits the second biological data to the recording apparatus 20 via the network NT2. Note that the processing unit 520 reads seat information and the flight number of the airplane X, which are described on a ticket for the airplane X which is owned by the customer 102, by using a scanner (not illustrated), for example, and may thereby acquire the seat identifier and the flight number identifier.

The communication unit 530 is configured with a communication apparatus that connects the second biological information acquisition apparatus 50 with the network NT2 by using wireless communication such as Wi-Fi® or wired communication, for example. The communication unit 530 transmits the second biological data (hereinafter referred to as "second saved biological data") that are associated with the flight number identifier and the seat identifier to the recording apparatus 20 under control of the processing unit 520. Note that in the second embodiment, the saved biological data that are generated by the first biological information acquisition apparatus 10A will be referred to as first saved biological data.

FIG. 14 is a diagram that illustrates one example of a data configuration of a first saved biological table T11 in which the first saved biological data are registered in the second embodiment of the present disclosure. In the first saved biological table T11, the difference from the saved biological table T1 illustrated in FIG. 3 is only a point that "biological data" becomes "first biological data", and no fundamental difference is present.

FIG. 15 is a diagram that illustrates one example of a data configuration of the second saved biological data according to the second embodiment of the present disclosure. The second saved biological data include fields of "flight number identifier", "seat identifier", and "second biological data". Note that in the second saved biological data, the difference from the first saved biological data illustrated in FIG. 14 is only a point that "first biological data" becomes "second biological data", and no fundamental difference is present.

FIG. 13 will be referred to again. In the second embodiment, the biological data management unit 210 generates the attendant-associated data by associating the second biological data included in the second saved biological data with the first saved biological data, and stores the attendant-associated data in the attendant-associated data storage unit 220.

FIG. 16 is a diagram that illustrates one example of a data configuration of an attendant-associated table T31 in which the attendant-associated data are registered according to the second embodiment of the present disclosure. In the attendant-associated table T31, the different point from the attendant-associated table T3 illustrated in FIG. 6 is a point that a field of "second biological data" is further added.

The biological data management unit 210 specifies the first saved biological data that have the same "flight number identifier" and "seat identifier" as "flight number identifier" and "seat identifier" in the second saved biological data, associates the second biological data included in the second saved biological data with the specified first saved biological data, and may thereby generate the attendant-associated data.

Figure 17:
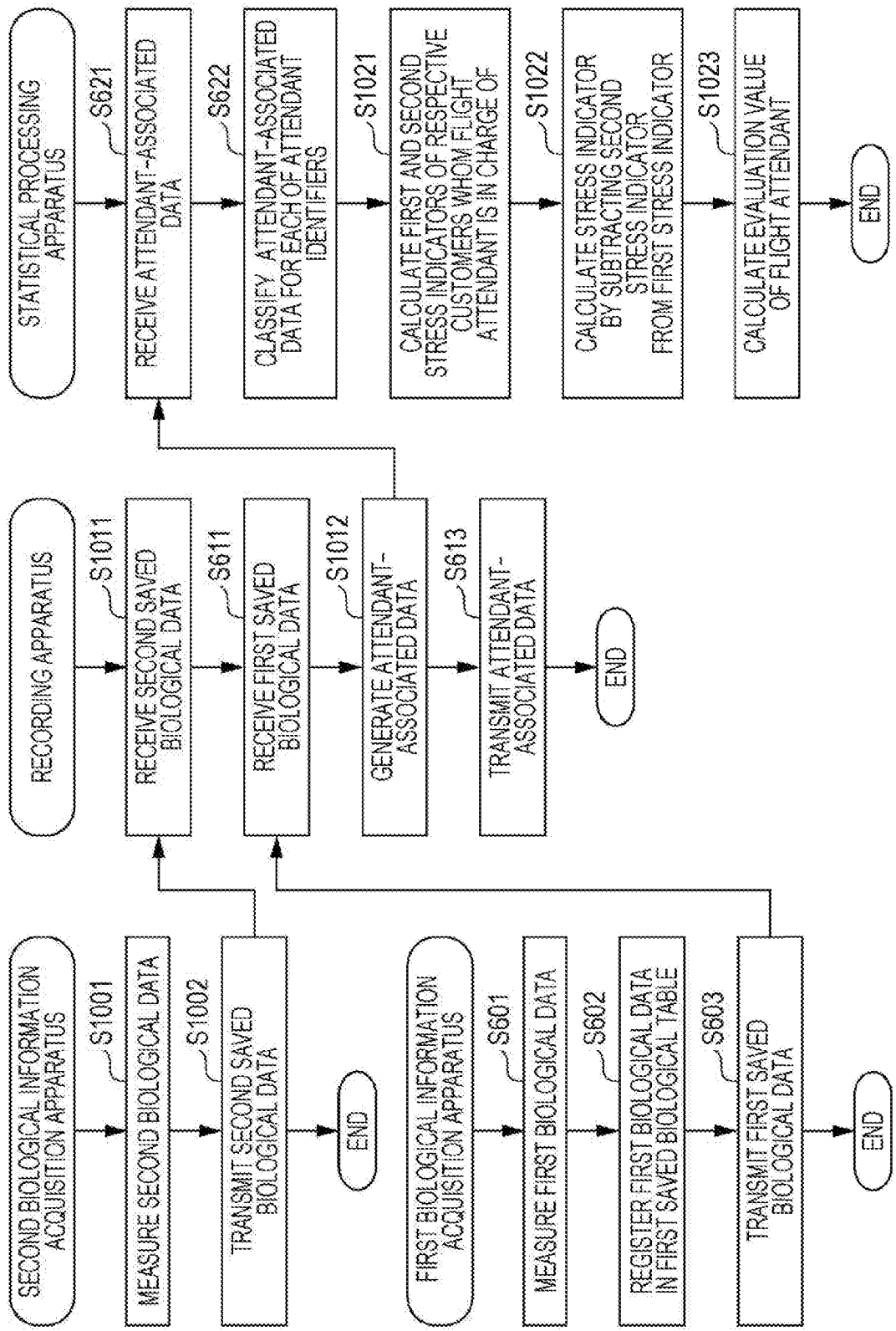
FIG. 17 is a flowchart that illustrates one example of a process from measurement of the first and second biological data to calculation of the evaluation value in the flight attendant evaluation system according to the second embodiment of the present disclosure.

FIG. 17 is a flowchart that illustrates one example of a process from measurement of the first and second biological data to calculation of the evaluation value in the flight attendant evaluation system 1A according to the second embodiment of the present disclosure. Note that in FIG. 17, the same reference characters are given to the same processes as FIG. 10, and a description will not be made.

First, the biological sensor 510 of the second biological information acquisition apparatus 50 measures the second biological data of the customer 102 who passes through the boarding gate 501 (S1001). Next, the processing unit 520 of the second biological information acquisition apparatus 50 generates the second saved biological data by associating the second biological data measured in S1001 with "flight number identifier" and "seat identifier", and transmits the second saved biological data to the recording apparatus 20 by using the communication unit 530 (S1002).

Next, the communication unit 230 of the recording apparatus 20 receives the second saved biological data (S1011). Then, the process of S611 is executed similarly to the first embodiment. Next, the biological data management unit 210 of the recording apparatus 20 generates the attendant-associated data by associating the second biological data included in the received second saved biological data with the corresponding first saved biological data, and registers the attendant-associated data in the attendant-associated table T31 (S1012).

In S1021 that follows S622, the evaluation value calculation unit 310 of the statistical processing apparatus 30 calculates first and second stress indicators of the customers 102 who on board sit on the seats 101 which each of the flight attendants is in charge of from the first and second biological data included in the classified attendant-associated data.

In the example of FIG. 16, with respect to the flight attendant of the attendant identifier "J01", the first stress indicator that corresponds to first biological data VT11 is calculated, and the first stress indicator that corresponds to the biological data VT13 is calculated. Similarly, with respect to the flight attendant of the attendant identifier "J01", the second stress indicator that corresponds to second biological data VT21 is calculated, and the second stress indicator that corresponds to biological data VT23 is calculated. Note that the first and second stress indicators are calculated by using the same scheme as the stress indicator described in the first embodiment.

Next, the evaluation value calculation unit 310 calculates the stress indicator for each piece of the attendant-associated data by subtracting the second stress indicator from the first stress indicator for each piece of the attendant-associated data (S1022). One example of a calculation process of the stress indicator will be described by using the attendant-associated table T31 in the first row in FIG. 16. The evaluation value calculation unit 310 calculates the stress indicator with respect to the attendant-associated data in the first row by subtracting the second stress indicator calculated from the second biological data VT21 from the first stress indicator calculated from the first biological data VT11. The evaluation value calculation unit 310 performs a similar process for the other pieces of attendant-associated data, and thereby calculates the stress indicators.

Next, the evaluation value calculation unit 310 calculates the average of the stress indicators calculated in S1022 for each of the flight attendants as the evaluation value of each of the flight attendants (S1023), and registers the evaluation value in the evaluation table T4.

As the stress to the customer 102 who is boarded on the airplane X increases, the difference between the first stress indicator and the second stress indicator increases. Furthermore, because the stress indicator obtained from the difference is based on the stress indicator at a time before the customer 102 boards the airplane X as a reference, it may be considered that the stress indicator accurately reflects the influence of the stress that is given to the customer 102 by the airplane X. Accordingly, in this embodiment, the evaluation value is calculated by using the stress indicator that is obtained by subtracting the second stress indicator from the first stress indicator.

In such a manner, in the flight attendant evaluation system 1A according to the second embodiment, the stress indicator is calculated based on the difference between the second stress indicator calculated from the second biological data at a time before the customer 102 boards the airplane X and the first stress indicator calculated from the first biological data of the customer 102 who has boarded the airplane X. Thus, the stress indicator may accurately be calculated.

Third Embodiment

A flight attendant evaluation system 1B according to a third embodiment has characteristics that the evaluation of the flight attendant who performs service which raises the stress for a second customer who is more important than a first customer is lowered and the evaluation of the flight attendant who performs service which lowers the stress for the second customer is raised. The second customer is classified as a customer who sits on a special seat (for example, first class and business class) or a customer whose frequent flyer points are a certain value or more. The first customer is classified as the other customer than the second customer.

Note that in the third embodiment, the same reference characters will be given to the same configuration elements as the first embodiment, and a description will not be made. Further, the third embodiment is applicable to cases where the configurations of both of the first and second embodiments are employed. However, in the following description, a description will be made about an example where the configuration of the first embodiment is employed. Accordingly, in the flight attendant evaluation system 1B according to the third embodiment, the general configuration is the same as FIG. 1 and FIG. 2.

FIG. 2 will be referred to. In the third embodiment, with respect to the second customer, in a case where a stress indicator K1 calculated from the biological data is higher than a first threshold value TH1, the evaluation value calculation unit 310 of the statistical processing apparatus 30 decides an offset value α for increasing the stress indicator K1 as the difference between the stress indicator K1 and the first threshold value TH1 increases, and calculates a stress indicator K2 by correcting the stress indicator K1 by adding the offset value a to the stress indicator K1. Meanwhile, in a case where the stress indicator K1 is lower than a second threshold value TH2 (<TH1), the evaluation value calculation unit 310 decides an offset value β for decreasing the stress indicator K1 as the difference between the stress indicator K1 and the second threshold value TH2 increases, and calculates the stress indicator K2 by correcting the stress indicator K1 by subtracting the offset value β form the stress indicator K1.

Here, as the first threshold value TH1, an empirically obtained value may be employed at which the stress to the second customer is assumed to excess the stress in a usual condition in a case where the stress indicator K1 increases to the first threshold value TH1 or more. Further, as the second threshold value TH2, an empirically obtained value may be employed at which the stress to the second customer is assumed to fall below the stress in the usual condition and the second customer is assumed to be comfortable in a case where the stress indicator K1 decreases to the second threshold value TH2 or less.

The offset value α is decided by a function in which the value monotonically increases as a difference (K1−TH1), which results from the subtraction of the first threshold value TH1 from the stress indicator K1, increases, for example. The offset value β is decided by a function in which the value monotonically increases as a difference (TH2−K1), which results from the subtraction of the stress indicator K1 from the second threshold value TH2, increases, for example.

Figure 18:
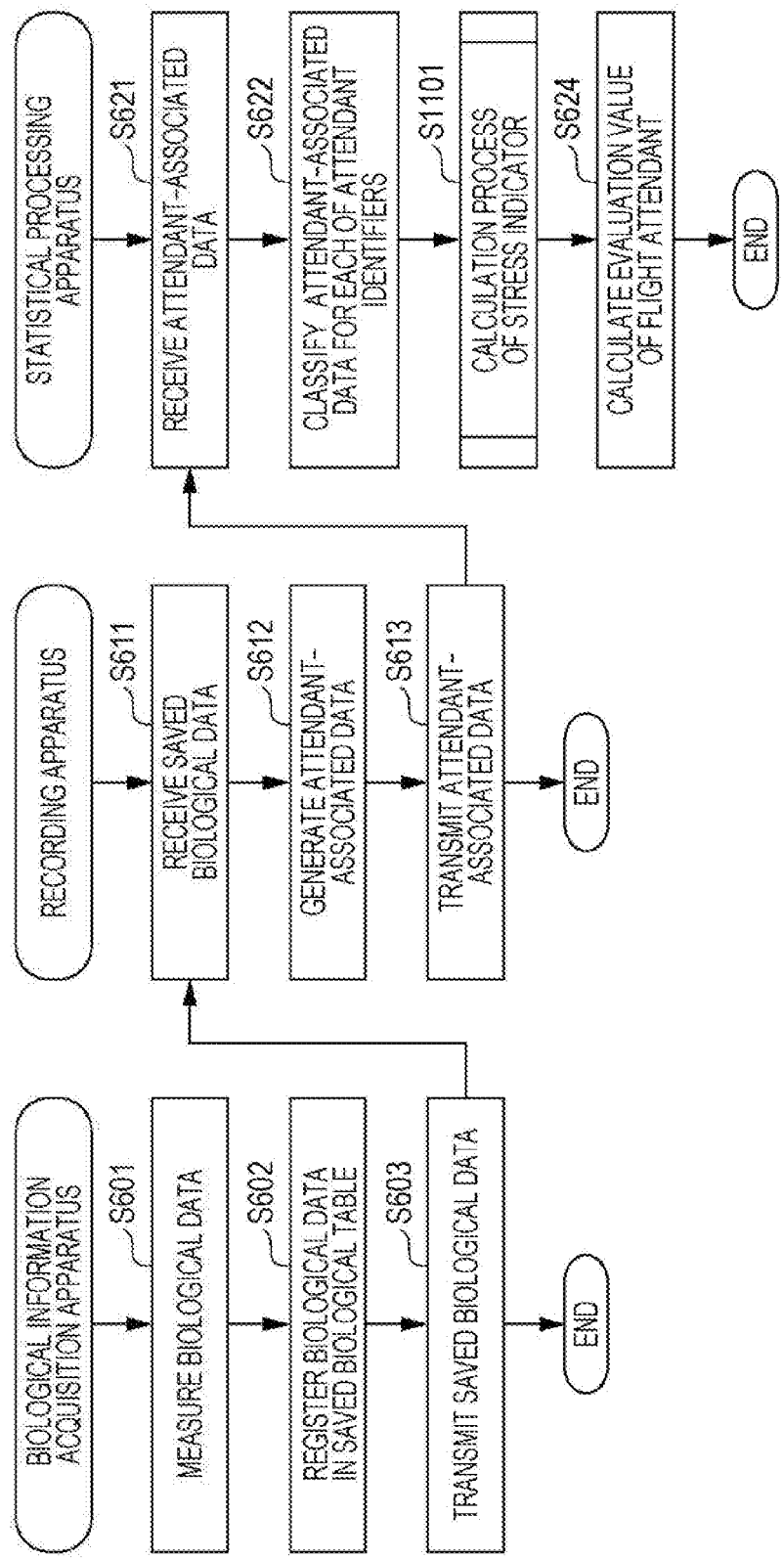
FIG. 18 is a flowchart that illustrates one example of a process from measurement of the biological data to calculation of the evaluation value in a flight attendant evaluation system according to a third embodiment of the present disclosure.

FIG. 18 is a flowchart that illustrates one example of a process from measurement of the biological data to calculation of the evaluation value in the flight attendant evaluation system 1B according to the third embodiment of the present disclosure. In FIG. 18, only the process of S1101 is different from FIG. 10. In S1101, the evaluation value calculation unit 310 of the statistical processing apparatus 30 executes an evaluation value calculation process.

Figure 19:
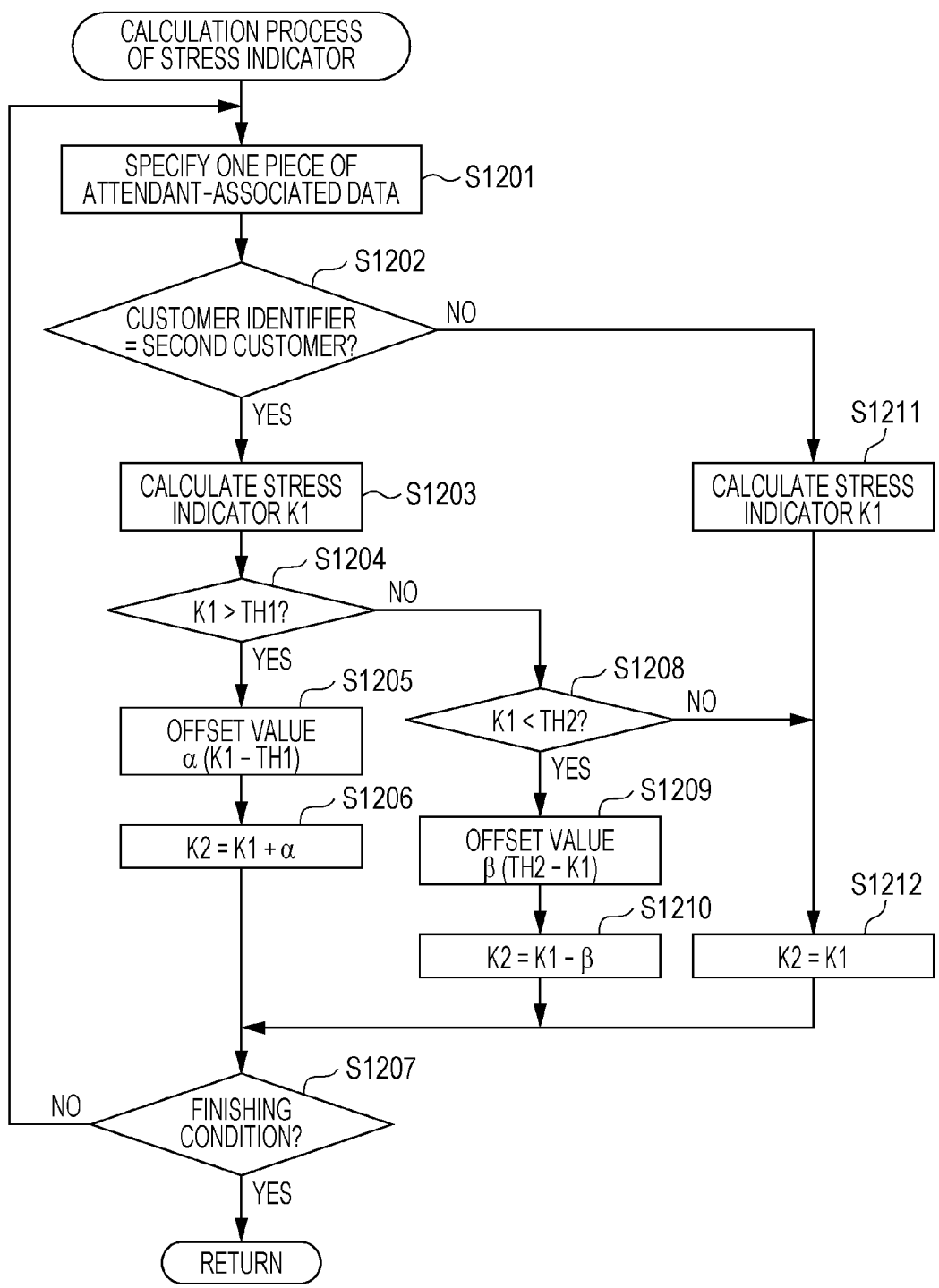
FIG. 19 is a flowchart that illustrates one example of an evaluation value calculation process illustrated in FIG. 18.

FIG. 19 is a flowchart that illustrates one example of the evaluation value calculation process indicated by S1101 of FIG. 18. First, the evaluation value calculation unit 310 specifies one piece of attendant-associated data to be a process target from the attendant-associated data that are classified for each of the attendant identifiers (S1201). Here, the evaluation value calculation unit 310 may specify one piece of attendant-associated data from the attendant-associated data that are classified for each of the attendant identifiers in a predetermined order (for example, a registration order).

Next, the evaluation value calculation unit 310 assesses whether a customer identifier included in the specified one piece of attendant-associated data is the customer identifier of the second customer. Here, the evaluation value calculation unit 310 refers to a reservation information table T6 (FIG. 20) that is in advance stored in the storage unit 330 and a customer table T7 (FIG. 21) that is in advance stored in the storage unit 330, and may thereby assess whether or not the concerned customer identifier is the customer identifier of the second customer.

FIG. 20 is a diagram that illustrates one example of a data configuration of the reservation information table T6 that is used in the flight attendant evaluation system 1B according to the third embodiment of the present disclosure. The reservation information table T6 is a database in which one piece of reservation information is registered in one record, and includes fields of "flight number identifier", "seat identifier", and "customer identifier". The reservation information is information that indicates which seat of which airplane flight is reserved with respect to each of the customers 102.

"Flight number identifier" and "seat identifier" are the same as FIG. 3. "Customer identifier" is data for uniquely identifying the customer to be a management target. In FIG. 20, the reservation information is registered which indicates that the customer 102 of the customer identifier "UO3" has reserved the seat of the seat identifier "line 3 A" for the airplane X of the flight number identifier "PAL485, Oct. 1, 2016, Airport A to Airport B".

Note that in the example of FIG. 20, only one piece of reservation information is illustrated. However, actually, pieces of reservation information for plural seats of plural airplanes X to be management targets are registered. Note that the reservation information table T6 is in advance stored in the storage unit 330 of the statistical processing apparatus 30.

FIG. 21 is a diagram that illustrates one example of a data configuration of the customer table T7 that is used in the flight attendant evaluation system 1B according to the third embodiment of the present disclosure. The customer table T7 is a database in which one piece of customer data is assigned to one record, and includes fields of "customer identifier", "name", "frequent flyer points" and "attribute". "Customer identifier" is the same as FIG. 20. In the field of "name", the name of the customer is registered. In the field of "frequent flyer points", the frequent flyer points possessed by the customer are registered. The frequent flyer points increases as the total distance in which the customer 102 boards airplanes of the concerned airline company increases, for example. In the field of "attribute", the data that indicate whether or not the customer has the attribute of the second customer are registered. Here, in a case where "premium" is registered in the field of "attribute", the customer is the second customer. Here, the attribute of "premium" is given to the customer whose frequent flyer points are a certain value or more or whose frequency of boarding with the special seats is a certain value or more. Note that the customer who sits on the special seat may be treated as the second customer. In this case, whether or not the customer sits on the special seat may be specified by the seat identifier.

The evaluation value calculation unit 310 extracts "customer identifier" that corresponds to "flight number identifier" and "seat identifier", which are included in one piece of attendant-associated data, from the reservation information table T6. Then, the evaluation value calculation unit 310 refers to the customer table T7 and may thereby assess the concerned customer as the second customer in a case where "premium" is registered in the field of "attribute" of the customer data that correspond to the extracted "customer identifier". Alternatively, the evaluation value calculation unit 310 may assess the concerned customer as the second customer in a case where "seat identifier" included in one piece of attendant-associated data indicates the seat that matches the special seat which is in advance defined.

FIG. 19 will be referred to again. In a case where the customer identifier indicates the customer identifier of the second customer (YES in S1202), the evaluation value calculation unit 310 calculates the stress indicator K1 from the biological data included in one piece of attendant-associated data (S1203). On the other hand, in a case where the customer identifier does not indicate the customer identifier of the second customer (NO in S1202), the evaluation value calculation unit 310 assesses the concerned customer as the first customer and causes the process to progress to S1211.

In S1204, in a case where the stress indicator K1 is higher than the first threshold value TH1 (YES in S1204), the evaluation value calculation unit 310 decides the offset value α from the difference (K1−TH1) (S1205). On the other hand, in a case where the stress indicator K1 is the first threshold value TH1 or lower (NO in S1204), the process progresses to S1208.

In S1206, the evaluation value calculation unit 310 calculates the stress indicator K2 by adding α to K1. Here, the offset value α increases as the difference (K1−TH1) increases. Thus, the stress indicator K2 increases as the amount by which the stress indicator K1 exceeds the first threshold value TH1 increases, that is, as the stress to the second customer increases. Thus, correction is made such that the stress indicator K1 of the flight attendant who is in charge of this second customer increases, and the evaluation value of this flight attendant lowers.

In S1208, in a case where the stress indicator K1 is lower than the second threshold value TH2 (YES in S1208), the evaluation value calculation unit 310 decides the offset value β from the difference (TH2−K1) (S1209). Next, the evaluation value calculation unit 310 calculates the stress indicator K2 by subtracting β from K1 (S1210). Here, the offset value β increases as the difference (TH2−K1) increases. Thus, the stress indicator K2 lowers as the stress to the second customer lowers. Thus, correction is made such that the stress indicator K1 of the flight attendant who is in charge of this second customer decreases, and the evaluation value of this flight attendant rises.

In S1211, the evaluation value calculation unit 310 calculates the stress indicator K1 from the biological data included in one piece of attendant-associated data. Next, the evaluation value calculation unit 310 calculates the stress indicator K1 that is calculated in S1211 or S1203 as the stress indicator K2 (S1212).

That is, with respect to the first customer, the stress indicator K1 is not corrected but is calculated as the stress indicator K2 with no change (NO in S1202, S1211, and S1212). Further, even with respect to the second customer, in a case where the stress indicator K1 is the first threshold value or lower and the second threshold value or higher (NO in S1204 and NO in S1208), the stress indicator K1 is not corrected but is calculated as the stress indicator K2 with no change.

In S1207, in a case where the attendant-associated data for which the stress indicator K2 is not yet calculated are present, the evaluation value calculation unit 310 assesses that a finishing condition is not satisfied (NO in S1207) and causes the process to return to S1201. On the other hand, in a case where the attendant-associated data for which the stress indicator K2 is not yet calculated are not present, the evaluation value calculation unit 310 assesses that the finishing condition is satisfied (YES in S1207) and finishes the process.

In such a manner, in the third embodiment, the evaluation of the flight attendant with respect to the second customer may be made more strict than the evaluation of the flight attendant with respect to the first customer.

The present disclosure may employ the following modifications.

(1) In the first to third embodiments, because the evaluation value is defined to increase as the stress indicator becomes higher, the evaluation value indicates that the evaluation becomes lower as the value increases. The present disclosure is not limited to this, but the evaluation value may be defined to increase as the stress indicator becomes lower. In this case, as the evaluation value, the average value of the reciprocals of the stress indicators for each of the flight attendants may be employed.

(2) In the first to third embodiments, the average value of the stress indicators is employed as the evaluation value. However, the present disclosure is not limited to this, but the deviation value of the average value of the stress indicators may be employed as the evaluation value.

(3) In the first to third embodiments, the recording apparatus 20, the statistical processing apparatus 30, and the evaluation display apparatus 40 are configured with different computers. However, the present disclosure is not limited to this, but the recording apparatus 20, the statistical processing apparatus 30, and the evaluation display apparatus 40 may be configured with one computer.

(4) In the above embodiments, a description is made that the sensor which uses the millimeter-wave radar or the pressure sensing tube may be employed as the biological sensor 110. However, the present disclosure is not limited to this.

For example, Japanese Patent No. 5735592 discloses that the comfortableness of a user is evaluated by 10 levels of −5 to +5 from the biological data such as a heart rate, a pulse, and a body temperature. Accordingly, in the present disclosure, the comfortableness disclosed in Japanese Patent No. 5735592 may be employed as the stress indicator. In this case, the stress indicator may be calculated from a brain wave, a brain blood flow, a pulse wave, a blood pressure, a respiration rate, the body temperature, and a sweat rate.

Further, Japanese Unexamined Patent Application Publication No. 2012-249797 discloses that a value that results from a linear combination of the heart rate, the body temperature, the blood pressure, and the sweat rate is calculated as the stress value. Accordingly, in the present disclosure, the stress value disclosed in Japanese Unexamined Patent Application Publication No. 2012-249797 may be employed as the stress indicator.

Further, for example, Japanese Unexamined Patent Application Publication (Translation of PCT Application) No. 2003-534864 discloses a technique for assessing the stress to a person by using thermal image data of a face of the person. Accordingly, in the present disclosure, the stress indicator may be calculated by using the technique disclosed in Japanese Unexamined Patent Application Publication (Translation of PCT Application) No. 2003-534864.

(5) In the first to third embodiments, the evaluation display apparatus 40 is provided on the outside of the airplane X but may be provided on the inside of the airplane X. In this case, the flight attendant evaluation system may calculate the evaluation value of the flight attendant in real time and cause the evaluation display apparatus 40 to present the evaluation value. In addition, in this case, the statistical processing apparatus 30 may calculate the evaluation value of each of the flight attendants by using only the biological data of the customers 102 who are boarded in the present time.

The present disclosure enables a flight attendant to be evaluated by using biological data and is thus useful for an improvement in service by the flight attendant.

What is claimed is:

1. A system, comprising:
   a first biological sensor that measures a plurality of first biological data of a plurality of customers;
   a storage that stores a plurality of attendant-associated data records, each attendant-associated data record including the first biological data of a customer of the plurality of customers, a seat identifier, and an attendant identifier associated with each other, the seat identifier indicating a seat of the customer, the attendant identifier indicating a flight attendant in charge of the seat;
   a processor that:
      calculates at least one stress indicator of at least one customer based on at least one attendant-associated data record extracted from the plurality of attendant-associated data records stored in the storage, the extracted at least one attendant-associated data record including the first biological data of a customer, the seat identifier and a first attendant identifier, each of the at least one stress indicator being calculated based on the first biological data in one of the extracted at least one attendant-associated data record that is associated with the first attendant identifier,
      calculates an evaluation value indicated by the first attendant identifier based on the at least one stress indicator of the at least one customer, and
      stores, in the storage, the calculated evaluation value in association with the first attendant identifier,
      wherein, in the calculating of the at least one stress indicator, a stress indicator is calculated for each of the extracted at least one attendant-associated data record for which a stress indicator has not calculated, and
      in the calculating of the evaluation value, the evaluation value is updated based on the evaluation value stored in the storage, and the calculated stress indicator.

2. The system according to claim 1, wherein the processor calculates an average value of the at least one stress indicator of the at least one customer calculated based on the extracted at least one attendant-associated data record, as the evaluation value.

3. The system according to claim 1, further comprising:
   a display that presents the evaluation value in a case where an output instruction for evaluation of a flight attendant is detected.

4. The system according to claim 1, wherein the processor performs correction that adds a greater offset value to the stress indicator as the stress indicator is greater in a case where the stress indicator of the customer satisfying a predetermined condition is greater than a first threshold value, and calculates the evaluation value based on the corrected stress indicator.

5. The system according to claim 1, wherein the processor performs correction that subtracts a greater offset value from the stress indicator as the stress indicator is smaller in a case where the stress indicator of the customer satisfying a predetermined condition is smaller than a second threshold value, and calculates the evaluation value based on the corrected stress indicator.

6. The system according to claim 1, further comprising:
   a second biological sensor that measures a plurality of second biological data of the plurality of customers before boarding, wherein
   the storage further stores the second biological data associated with the first biological data as in the attendant-associated data records, and
   the processor calculates each of the at least one stress indicator based on a difference between a first stress indicator and a second stress indicator, the first stress indicator being calculated based on the first biological data in one of the extracted at least one attendant-associated data record, the second stress indicator being calculated based on the second biological data in the one of the extracted at least one attendant-associated data record.

7. A method comprising:
   measuring a plurality of first biological data of a plurality of customers,
   storing in a storage, a plurality of attendant-associated data records, each attendant-associated data record including the first biological data of a customer of the plurality of customers, a seat identifier, and an attendant identifier associated with each other, the seat identifier indicating a seat of the customer, the attendant identifier indicating a flight attendant in charge of the seat,
   calculating at least one stress indicator of at least one customer based on at least one attendant-associated data record extracted from the plurality of attendant-associated data records stored in the storage, the extracted at least one attendant-associated data record including the first biological data of a customer, the seat identifier and a first attendant identifier, each of the at least one stress indicator being calculated based on the first biological data in one of the extracted at least one attendant-associated data record that is associated with the first attendant identifier,
   presenting, to a display, an evaluation value indicated by the first attendant identifier calculated based on the at least one stress indicator of the at least one customer, and
   storing, in the storage, the calculated evaluation value in association with the first attendant identifier,
   wherein, in the calculating of the at least one stress indicator, a stress indicator is calculated for each of the extracted at least one attendant-associated data record for which a stress indicator has not calculated, and
   in the presenting of the evaluation value, the evaluation value is updated based on the evaluation value stored in the storage, and the calculated stress indicator.

8. A method comprising:
   measuring a plurality of first biological data of a plurality of customers,
   storing in a storage, a plurality of attendant-associated data records, each attendant-associated data record including the first biological data of a customer of the plurality of customers, a seat identifier, and an attendant identifier associated with each other, the seat identifier indicating a seat of the customer, the attendant identifier indicating a flight attendant in charge of the seat,
   calculating at least one stress indicator of at least one customer based on at least one attendant-associated data record extracted from the plurality of attendant-associated data records stored in the storage, the extracted at least one attendant-associated data record including the first biological data of a customer, the seat identifier and a first attendant identifier, each of the at least one stress indicator being calculated based on the first biological data in one of the extracted at least one attendant-associated data record that is associated with the first attendant identifier, calculating an evaluation value indicated by the first attendant identifier based on the at least one stress indicator of the at least one customer, and storing, in the storage, the calculated evaluation value in association with the first attendant identifier, wherein, in the calculating of the at least one stress indicator, a stress indicator is calculated for each of the extracted at least one attendant-associated data record for which a stress indicator has not calculated, and in the calculating of the evaluation value, the evaluation value is updated based on the evaluation value identified stored in the storage, and the calculated stress indicator.

9. The system according to claim 1, wherein the evaluation value is updated by calculating an average value of the stored evaluation value stored in the storage and the calculated stress indicator.

10. The method according to claim 7, wherein the evaluation value is updated by calculating an average value of the stored evaluation value stored in the storage and the calculated stress indicator.

11. The method according to claim 8, wherein the evaluation value is updated by calculating an average value of the evaluation value stored in the storage and the calculated stress indicator.

12. The system according to claim 1, wherein the evaluation value of a flight attendant indicated by the first attendant identifier is calculated based on the at least one stress indicator of the at least one customer.

13. The method according to claim 7, wherein the evaluation value of a flight attendant indicated by the first attendant identifier is calculated based on the at least one stress indicator of the at least one customer.

14. The method according to claim 8, wherein the evaluation value of a flight attendant indicated by the first attendant identifier is calculated based on the at least one stress indicator of the at least one customer.

15. The system according to claim 1, wherein the processor further classify the plurality of attendant-associated data records stored in the storage for each attendant identifier, and the processor calculates the at least one stress indicator of the at least one customer based on the extracted at least one attendant-associated data record, which is classified for the first attendant identifier.

16. The system according to claim 1, wherein the attendant-associated data record does not include biological data of the flight attendant indicated by the attendant identifier, and the evaluation value is calculated without using biological data of the flight attendant.

* * * * *